United States Patent
Zhang et al.

(10) Patent No.: US 8,742,175 B2
(45) Date of Patent: Jun. 3, 2014

(54) PARA—OR MESO-FUNCTIONALIZED AROMATIC KETONE COMPOUNDS, PREPARATION METHODS THEREOF, AND PHOTOPOLYMERIZATION INITIATORS COMPRISING THE SAME

(75) Inventors: Yongbo Zhang, Shenzhen (CN); Yanchao Wang, Shenzhen (CN); Yapeng Wang, Shenzhen (CN); Huaihai Song, Shenzhen (CN); Zhigang Wang, Shenzhen (CN)

(73) Assignee: Shenzhen UV-Chemtech Co., Ltd., Shenzhen (CN)

( * ) Notice: Subject to any disclaimer, the term of this patent is extended or adjusted under 35 U.S.C. 154(b) by 0 days.

(21) Appl. No.: 13/695,600

(22) PCT Filed: Nov. 4, 2011

(86) PCT No.: PCT/CN2011/001866
§ 371 (c)(1),
(2), (4) Date: Oct. 31, 2012

(87) PCT Pub. No.: WO2012/062041
PCT Pub. Date: May 18, 2012

(65) Prior Publication Data
US 2013/0217877 A1   Aug. 22, 2013

(30) Foreign Application Priority Data
Nov. 12, 2010   (CN) .......................... 2010 1 0543143

(51) Int. Cl.
*C07C 49/00*   (2006.01)
*C07C 45/00*   (2006.01)
*C07C 211/00*   (2006.01)
*C07C 217/00*   (2006.01)
*C07C 261/00*   (2006.01)

(52) U.S. Cl.
USPC ........... 568/312; 568/316; 564/370; 564/384; 564/391; 560/26

(58) Field of Classification Search
USPC .................. 568/312, 316; 564/370, 384, 391; 560/26, 127, 221
See application file for complete search history.

(56) References Cited

U.S. PATENT DOCUMENTS

| 4,739,052 A * | 4/1988 | Husler et al. ................... 544/174 |
| 5,091,586 A * | 2/1992 | Higuchi et al. ................ 568/332 |
| 5,286,750 A * | 2/1994 | Mueller et al. ................ 514/546 |
| 7,642,296 B2 * | 1/2010 | Husler et al. ...................... 522/6 |

* cited by examiner

*Primary Examiner* — Sikarl Witherspoon
(74) *Attorney, Agent, or Firm* — CBM Patent Consulting, LLC

(57) ABSTRACT

The present invention discloses novel aromatic ketone compounds with functional substitution groups at para- or meta positions which can be used as photo-initiators or effective components of photo-initiator mixtures for the photopolymerizations of ethylenically unsaturated systems. The preparation of these compounds is also disclosed.

14 Claims, No Drawings

PARA—OR MESO-FUNCTIONALIZED AROMATIC KETONE COMPOUNDS, PREPARATION METHODS THEREOF, AND PHOTOPOLYMERIZATION INITIATORS COMPRISING THE SAME

FIELD OF THE INVENTION

This invention concerns photo-initiator technical field. Disclosed herein are some novel functionalized aromatic ketone compounds featuring para- or meta-aromatic ring substitution patterns, their preparation methods, and their uses as photo-initiators or effective components of photo-initiator mixtures for the photopolymerizations of ethylenically unsaturated systems.

BRIEF DESCRIPTION OF BACKGROUND ART

For UV-curing materials it is known that some hydroxyarylketones and diaryl ketones are useful photo-initiators for the photopolymerizations of ethylenically unsaturated systems. As structured below, examples of hydroxyarylketone-type photo-initiators are so-called Darocur 1173 (2-hydroxy-2-methyl-1-phenylpropan-1-one) and Irgacure 184 ((1-hydroxycyclohexyl)(phenyl)methanone), and examples of diarylketone-type photo-initiators are benzophenone (BP) and [1,1'-biphenyl]-4-yl(phenyl)methanone (PBZ). These compounds are all commercially available and serve as some of the most important benchmark photo-initiators widely used today.

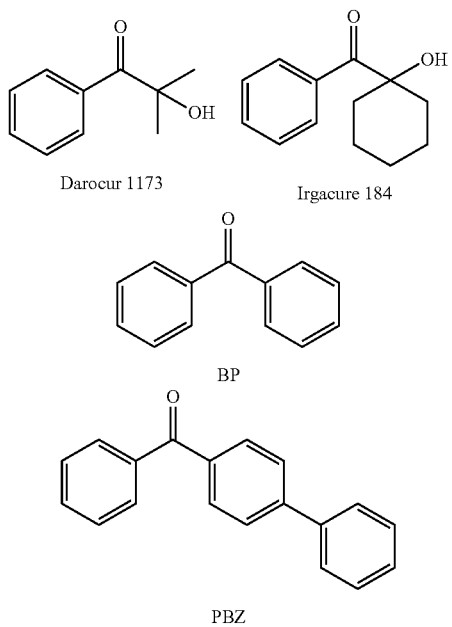

However, while functioning the relevant photochemical cleavage reactions of these compounds generally lead to emissions of various substances such as benzene, benzaldehyde, acetone, cyclohexanone etc, which are usually highly volatile, harmful, and even carcinogenic, and are thus sometimes classified as undesirable VOCs (abbreviation for Volatile Organic Compounds). Not surprisingly, environmental pollution as well as health threat issues arising from such harmful emissions have been experiencing increasing levels of public attention and legislative regulations. Consequently, several patent disclosures have been devoted to exploring potential solutions to these significant challeneges through designs and preparations of new compounds, for examples, Chinese patent applications CN1288123C, CN1529588A, CN1914560A, CN100548955C, CN100523007C, CN1832912A, CN1942424A, and United States patent applications US2006/0270748A1, 2010/0104979A1, US2005/0239971A1, and U.S. Pat. No. 4,739,052. As shown below, some representative chemical structures of such "new-generation" photo-initiator compounds are Irgacure 127 [1,1'-(methylenebis(4,1-phenylene))bis(2-hydroxy-2-methylpropan-1-one)] and bifunctional hydroxyketones A-C. It should be emphasized that, without any exception, in these reported structures the photo-active hydroxyketone functionality and the ring substituent always display para-aromatic ring substitution pattern. This is not surprising since the stepwise installation of hydroxyketone functionality to an aromatic ring must follow the principle of so-called Friedel-Crafts acylation reaction, that is, acylation on an aromatic ring bearing an electron-releasing substituent (such as an alkyl group) would occur at the site that is para- to that substituent.

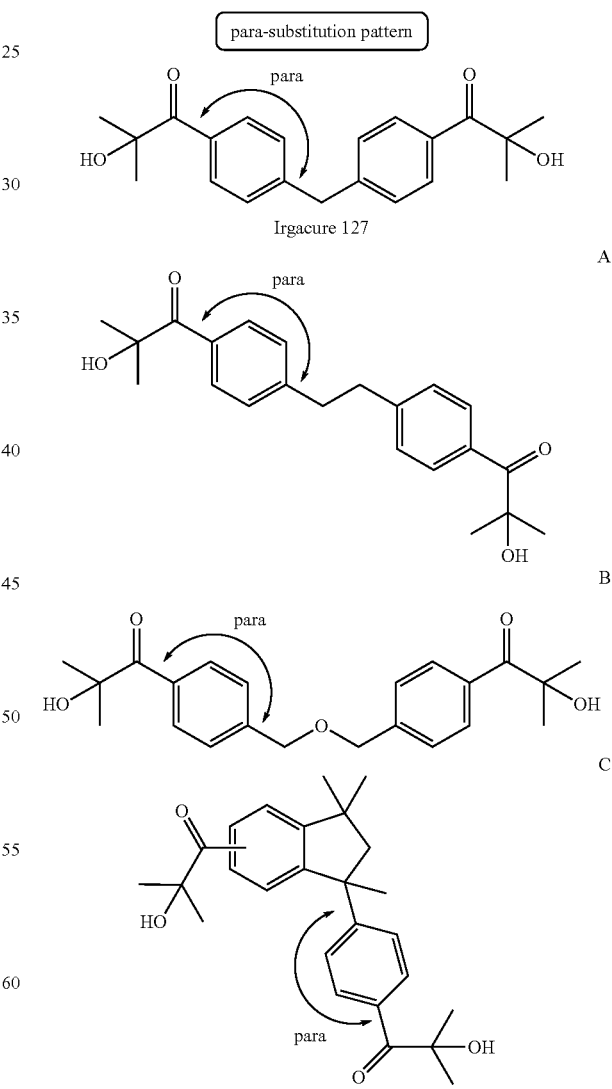

These known disclosures collectively reflect a strong market demand for developing new generations of environment as well as health-friendly photo-initiator products, particularly those that can help tackle the aforementioned drawbacks associated with the uses of conventional photo-initiators, including reduction or elimination of emissions of harmful VOCs, carcinogenic aromatic hydrocarbons, and unpleasant residual odors. Moreover, equally important measure of the potential usefulness of these new products is their practicality, i.e., they will have to address the above-mentioned challenges while at the same time maintain cost-effectiveness.

SUMMARY OF THE INVENTION

The present invention aims at introducing a series of novel functionalized aromatic ketone compounds featuring para- or meta-aromatic ring substitution patterns, their preparation methods, and their uses as photo-initiators or effective components of photo-initiator mixtures for the free-radical photopolymerizations of ethylenically unsaturated systems.

These said para- or meta-substituted functionalized aromatic ketone compounds have the following general structural formulae I-III:

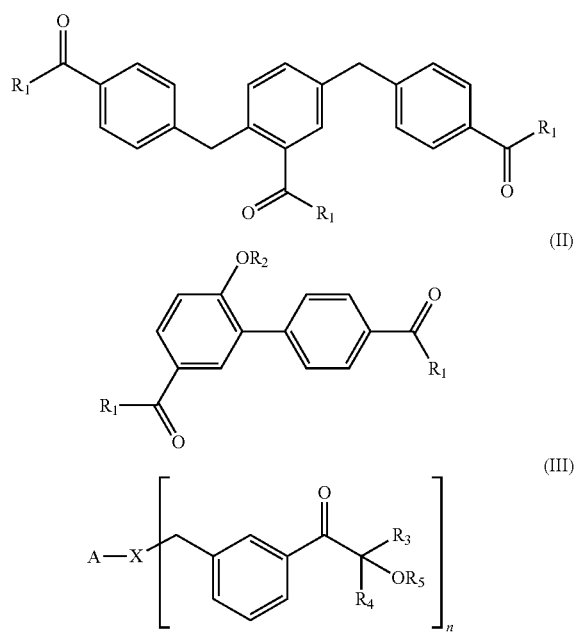

The present invention also discloses the relevant chemical preparation methods that are generally applicable towards the syntheses of the compounds summarized under structures I-III. The methods are illustrated below. For compounds of structures I-II, they take advantage of 1,4-dibenzylbenzene D and alkyl-substituted 2-phenyl-phenol E as the backbone skeleton G (i.e., G=D or E), respectively, for the implementations of desirable Friedel-Crafts acylation technologies and subsequent flexible conversions into hydroxyketones and diarylketones products.

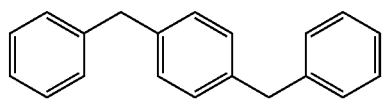

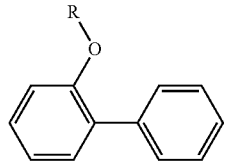

For compounds of structure III, the syntheses begin with a common hydroxyketone "building block" F, which is structurally such as the meta-chloromethylated Darocur 1173 [i.e., 1-(3-(chloromethyl)phenyl)-2-hydroxy-2-methylpropan-1-one]. This meta-chloromethylated Darocur 1173 can be conveniently prepared by subjecting Darocur 1173 under the dual actions of Lewis acid promoter and formaldehyde for an intended Friedel-Crafts alkylation reaction. Since the hydroxyketone functionality in Darocur 1173 itself represents a strongly electron-withdrawing substituent, the principle of Friedel-Crafts alkylation thus commands the chloromethylation event onto the aromatic ring position that is exclusively meta- to the hydroxyketone group.

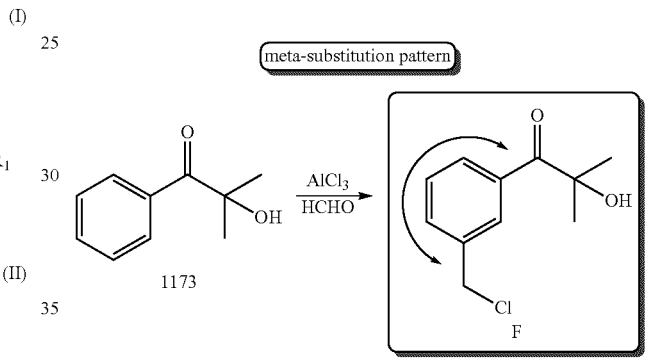

This represents a critical discovery, as it, for the first time, enables facile preparations of a series of new meta-substituted mono- or multi-functional hydroxyketones that would otherwise be impossible with known arts utilizing Friedel-Crafts acylation technologies. The important distinctions between the present invention and known arts therefore must be made with the two recognitions that: (a) while known photo-initiators in the literature were generally prepared with Friedel-Crafts acylations as the key strategic reactions and thus structurally universally follow para-substitution patterns, the present invention instead employs Friedel-Crafts alkylations and yields hydroxyketones featuring unique meta-structural pattern. (b) while known arts for preparing para-substituted hydroxyketones have to follow, to people technically skilled in the field, the general step-wise sequences of Friedel-Crafts acylation-halogenation-base hydrolysis, the present invention can access meta-substituted hydroxyketones in a much straightforward "building-block-enabled" approach, i.e., the needed photoactive hydroxyketone functionality was already in place at the very beginning and subsequent manipulations merely deal with installations of suitable linkages.

The present invention also discovered that the disclosed compounds under general formulae I-III function as effective photo-initiators or effective components of photo-initiator mixtures for the free-radical photopolymerizations of ethylenically unsaturated systems. These compounds and their uses are advantageous as compared to known arts since they are new chemical identities that are previously unknown or not possible to access with reported technologies, and as shown below they are useful and cost-effective as photoinitiators and furthermore they, while functioning, lead to eliminations or significant reductions of emissions of unpleasant VOCs.

Aromatic ketone compounds featuring para- or meta-substitution patterns disclosed in this invention follow the shown general structural formulae I-III:

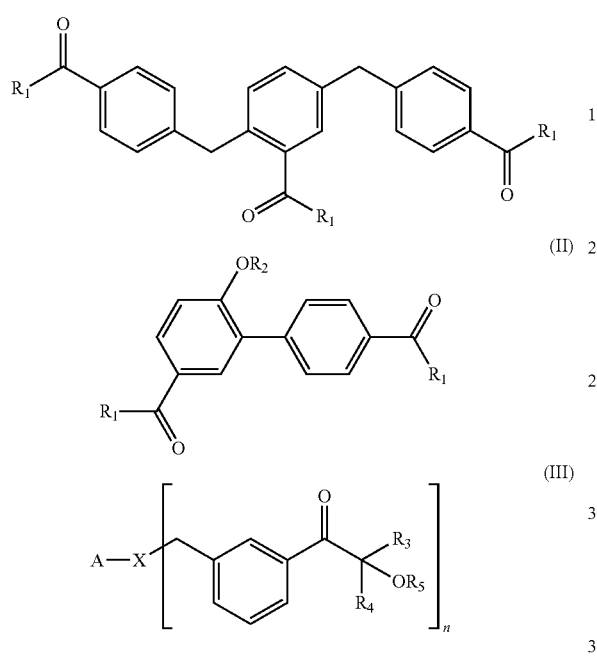

Wherein:
$R_1$ is one of the following two structures:

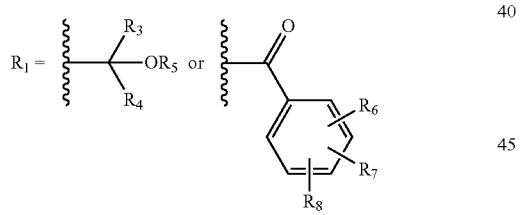

$R_2$, $R_3$, and $R_4$ are each independently of the others $C_1$-$C_{12}$ alkyl which may be branched or unbranched, may or may not contain ring structures, or $R_2$, $R_3$, and $R_4$ are each independently of the others $C_6$-$C_{12}$ aryl ring which may be substituted or unsubstituted. $R_2$, $R_3$, and $R_4$ may each independently of the others be interrupted by one to four O, N, Si, S, C(O), C(S), OC(O), OC(O)O, SC(O), SC(S), C(O)NH, C(O)NR$_x$, OP(O), OSiR$_x$R$_y$0, or carbon-carbon double bond or triple bond. $R_3$ and $R_4$ may form a cyclic ring structure. $R_5$ is hydrogen, $R_x$, Si(R$_x$)$_2$(R$_y$), or Si(R$_x$)$_3$; $R_6$, $R_7$, and $R_8$ are each independently of the others hydrogen or $R_x$, wherein $R_x$ or $R_y$ has the same definition as $R_2$, $R_3$, or $R_4$.

n is an integer from 1 to 6, preferably an integer from 1 to 4.

X is O, S, N, NH, or NR$_x$; A is a n-valent linkage, when n is 1, A-X is OH, OR$_x$, SR$_x$, NHR$_x$, N(R$_x$)$_2$, or quaternary ammonium cation of form (R$_x$)$_3$N$^+$ or (R$_x$)$_2$R$_y$N$^+$; when n is 2, 3, 4, 5, or 6, A-X is N, NR$_x$, or quaternary ammonium cation of form R$_x$N$^+$, R$_x$R$_y$N$^+$, or (R$_x$)$_2$N$^+$, or A-X—(H)$_n$ correspondingly represents a n-functional (i.e., di- or oligo-) alcohol, thiol, phenol, carboxylic acid, or amine.

Such n-functional alcohol, thiol, phenol, carboxylic acid, or amine may be selected from the following illustrative but not limiting structures:

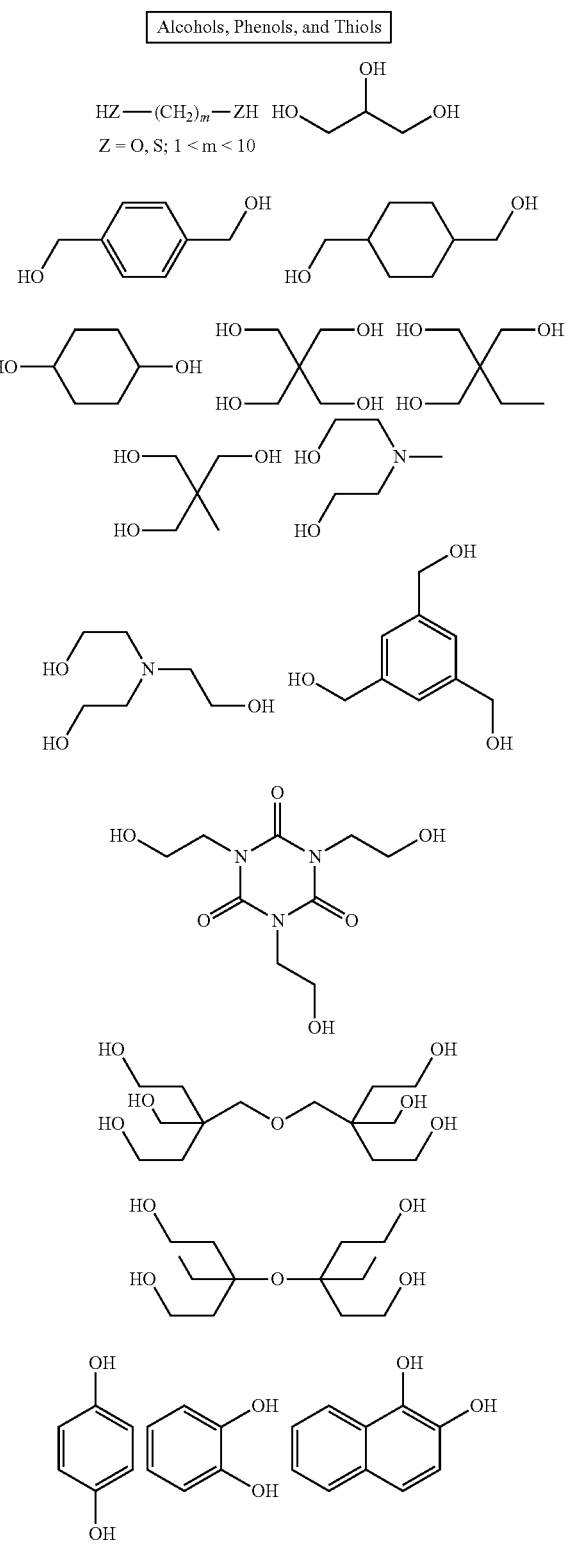

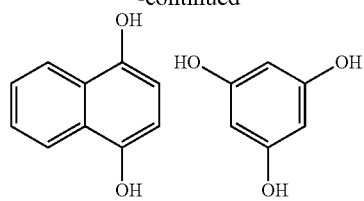
Carboxylic Acids
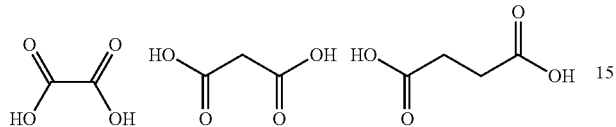
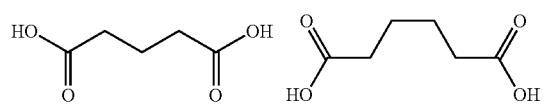
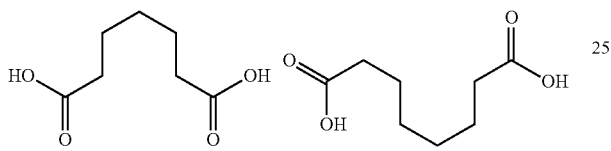
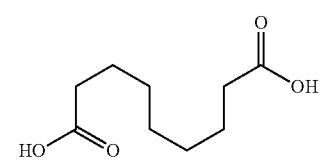
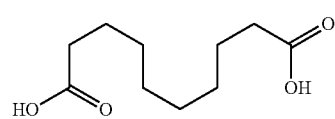
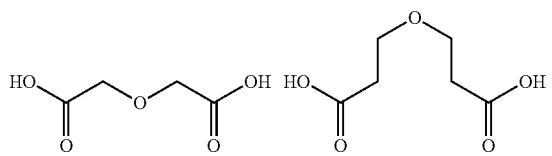
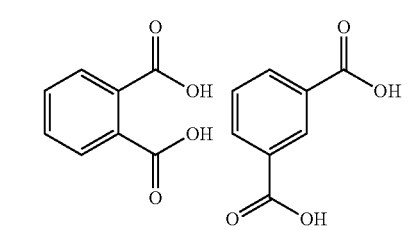
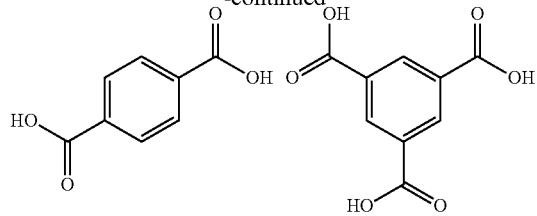
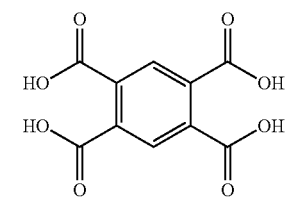
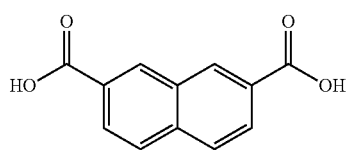
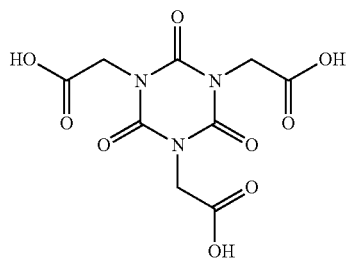
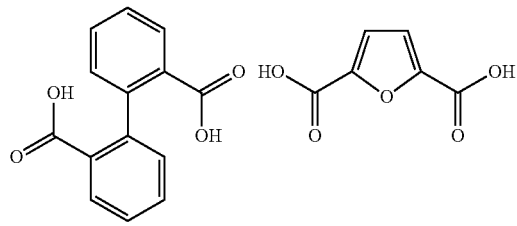
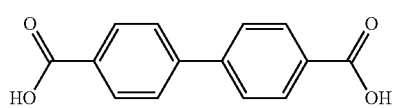
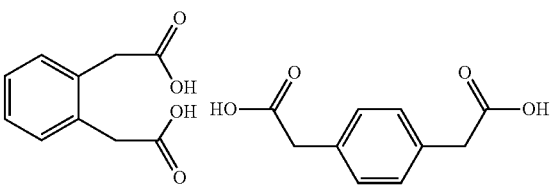
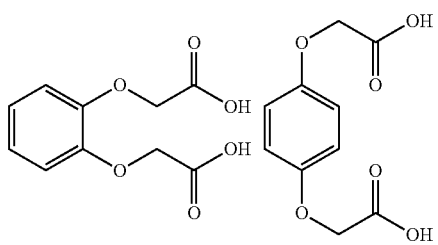

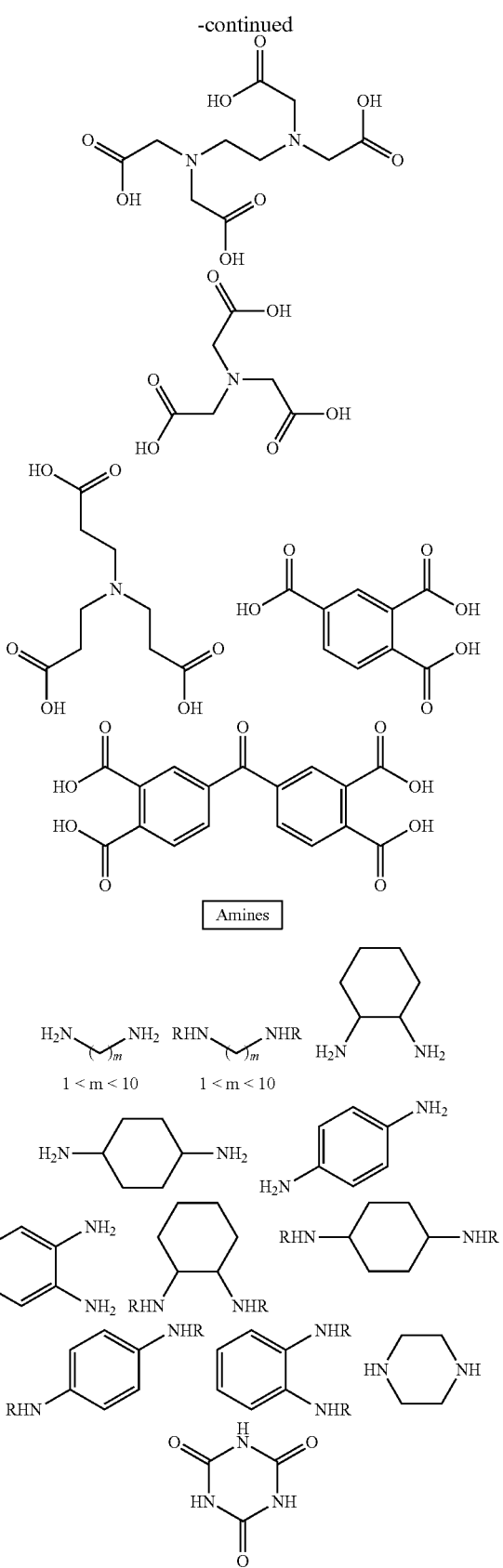

The present invention also discloses generally applicable methods for the preparations of compounds summarized under structural formulae I-III.

For compounds of formulae I-II, their preparations employ the Friedel-Crafts acylation reactions on two aromatic backbone skeletons: 1,4-dibenzylbenzene (D) and alkyl-substituted 2-phenyl-phenol (E), respectively. These acylated structures serve as common intermediates for flexible and facile preparations of the desired target compounds.

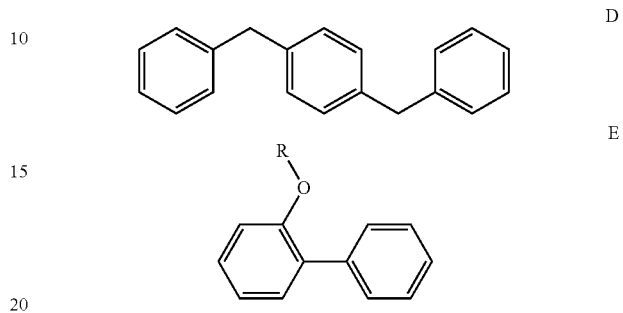

For compounds of formula III, the preparations leverage on the uses of a powerful common hydroxyketone "building block" such as F, which is structurally the meta-chloromethylated Darocur 1173 [i.e., 1-(3-(chloromethyl)phenyl)-2-hydroxy-2-methylpropan-1-one]. We had unexpectedly discovered that some hydroxyketone compounds, such as Darocur 1173, can be conveniently and site-specifically chloromethylated at the meta-position of its aryl ring through Friedel-Crafts alkylation reaction. This is fairly unusual because the hydroxyketone functionality on an aryl ring represents a strongly electron-withdrawing substituent that significantly de-activates that aryl ring, thus making such Friedel-Crafts electrophilic alkylations on a strongly electronically deficient aryl ring extremely difficult. As a matter of fact, although such meta-substituted aryl hydroxyketones clearly represent new types of chemical identities offering significantplication values, prior to this inventive disclosure, there is no report in the literature that teach how they might be synthetically accessed. The success of these transformations, as we had discovered and exemplified below, depends on intelligent combinations of proper Lewis acid promoters and reaction conditions control. Our findings have now permitted facile preparation of the versatile building block F through direct chloromethylation of Darocur 1173 under simple conditions.

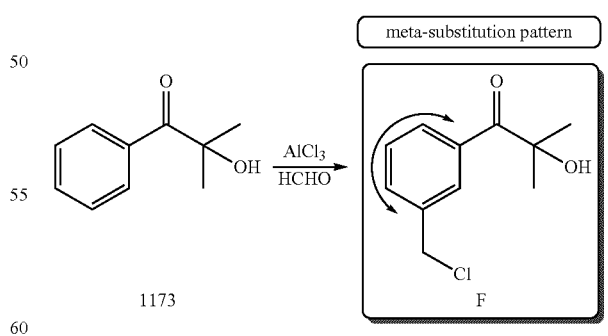

Because the chloromethyl group on an aryl ring is kown to be a highly versatile synthetic functionality, a wide variety of meta-substituted mono- and multi-functional hydroxyketones and their derivatives can thus be readily prepared in a "Building-Block-Enabled Approach" by employing transformations on for example the chloromethyl group in F that are routinely known to people skilled in the art. Some representative transformation equations are shown below (note that in the following reaction schemes the R group in the circle represents the structural unit A-X defined in the general formula III). In the presence of a proper promoter such as a base, F could readily condense with a range of carboxylic acids, amines, thiols, alcohols, or halides by means of substitution reactions to yield their corresponding products.

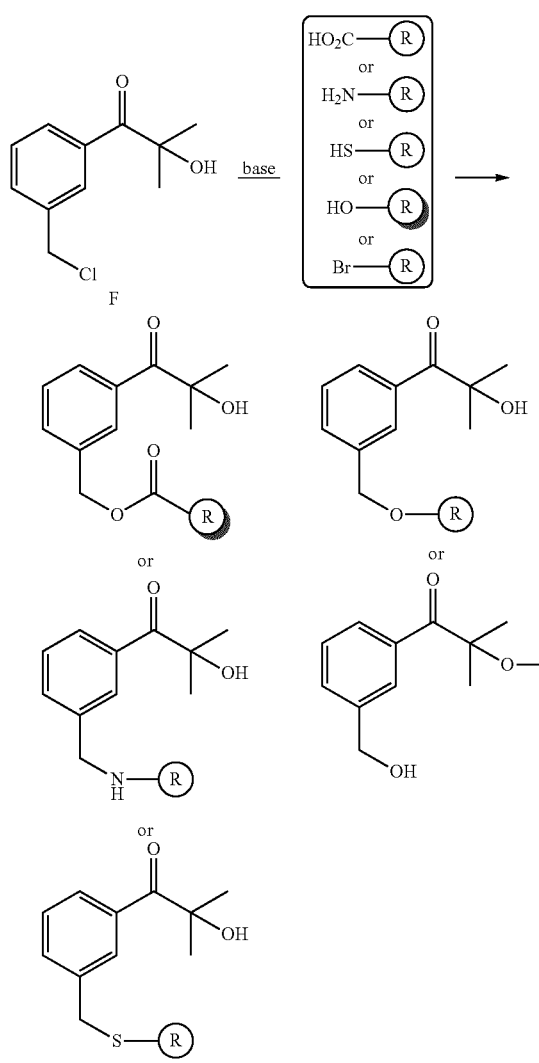

For compounds of formulae I-II, the said aryl backbone G is 1,4-dibenzylbenzene (D) and alkyl-substituted 2-phenylphenol (E), respectively. Both D and E themselves are known compounds, and their own preparation methods had been disclosed in literature [*Synthetic Communication*, 1995, 25, 2029; *Journal of the American Chemical Society*, 2002, 124, 9458]. As illustrated by the following reaction scheme, G can react with a range of acyl donors H by means of Friedel-Crafts acylations in the presence of Lewis acid reagents which include but are not limited to anhydrous $AlCl_3$, $FeCl_3$, $ZnCl_2$, or $La(OTf)_3$ where La denotes a rare-earth element. For some compounds under formulae I-II, such as those with $R_1$=—C(O)$C_6H_2R_6R_7R_8$ (i.e., diaryl ketone-type substances), the acylated compounds are just the target structures; but for other compounds under formulae I-II, such as those with $R_1$=—$CR_3R_4(OR_5)$, the acylated compounds need to undergo routine sequences of halogenations (chlorination or bromination) and base hydrolysis to yield the desired target products.

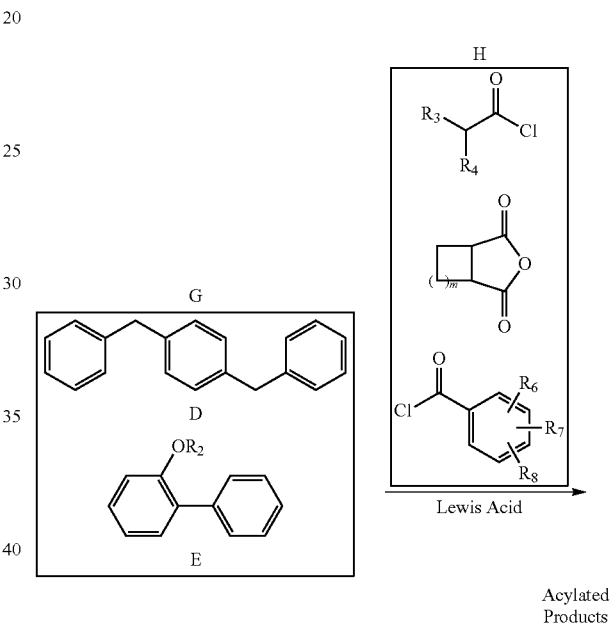

For compounds of formula III, their preparations starting from building block F, in addition to nucleophilic substitutions on its chloromethyl group illustrated above, can also take advantage of reaction chemistry on its hydroxyl group (as shown below), such as etherifications, esterifications, or silylation which are generally known technologies to skilled practitioners in the field.

General preparation strategies of compounds of formula (III)

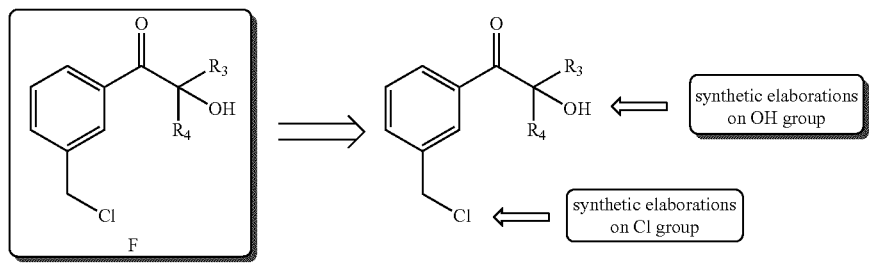

The following specific structures serve as selected but not limiting examples of compounds of formula I:
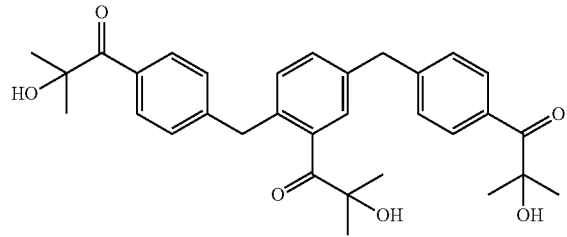
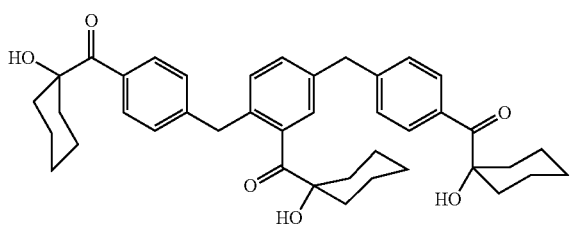
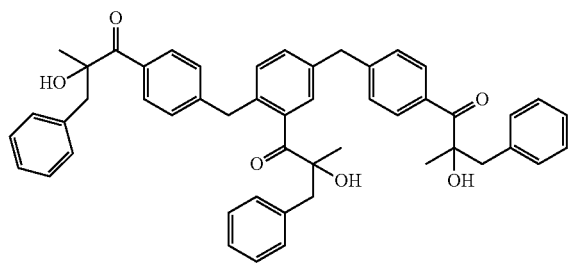
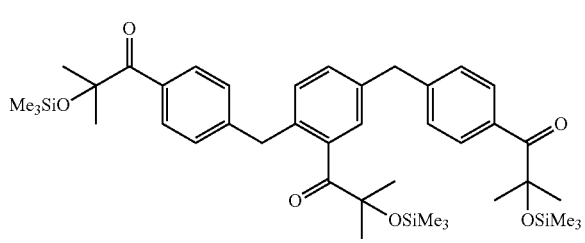
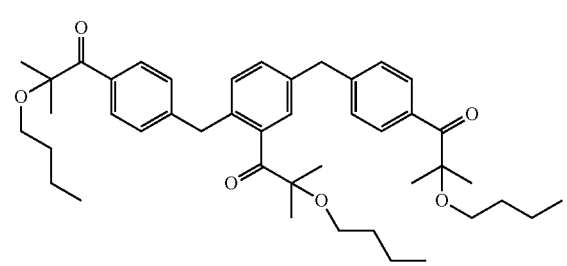
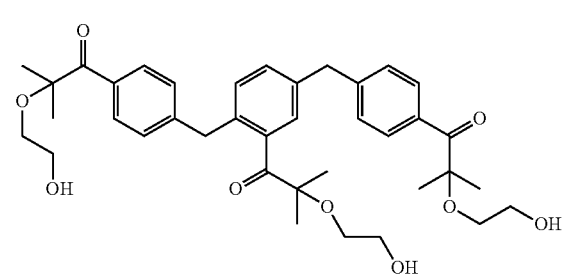
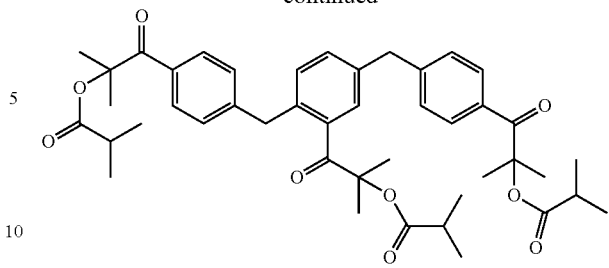
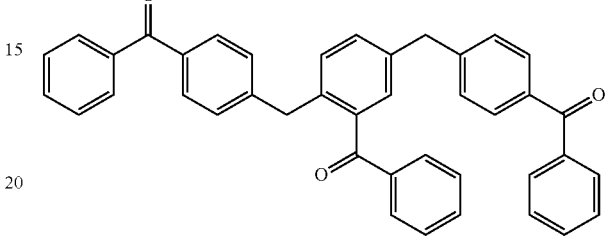
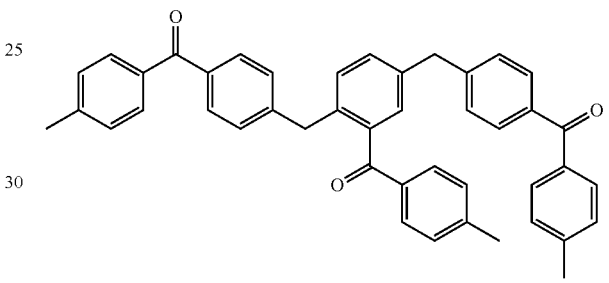
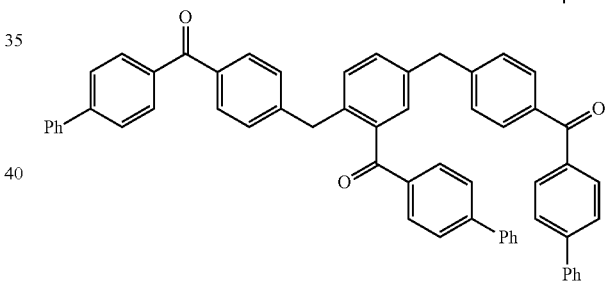
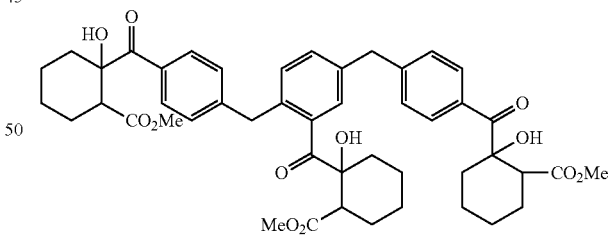
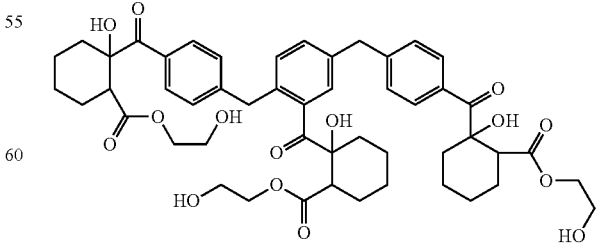
The following specific structures serve as selected but not limiting examples of compounds of formula II:

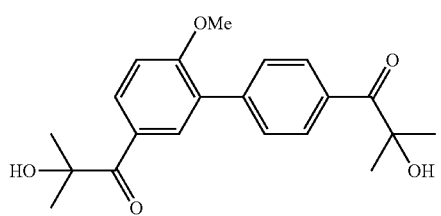
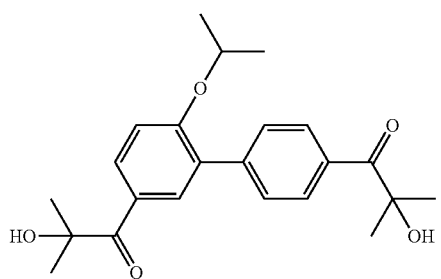
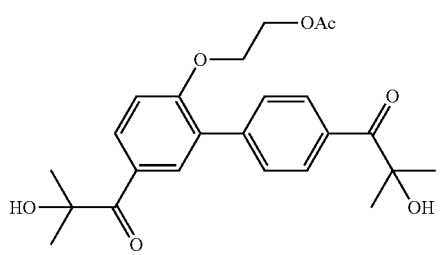
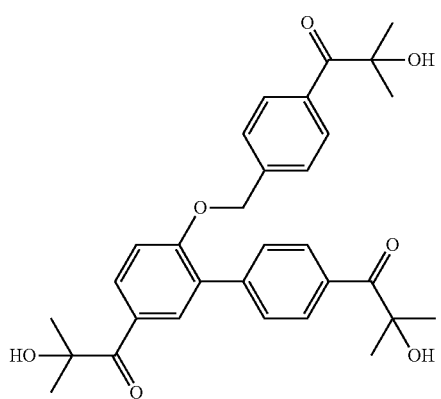
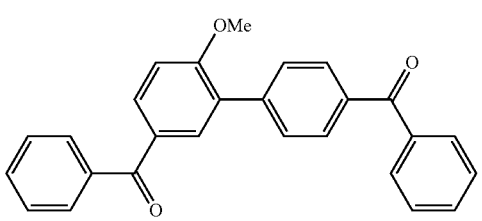
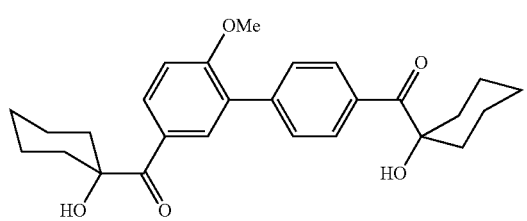
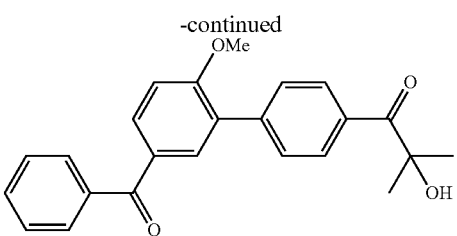
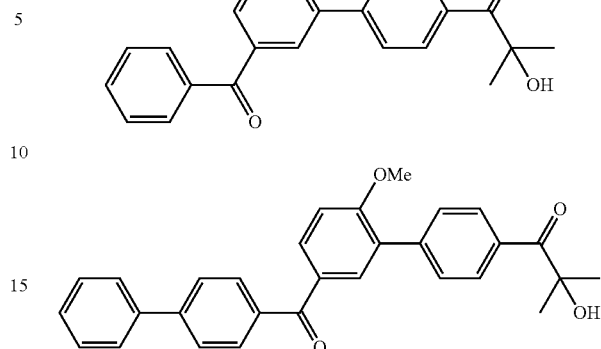
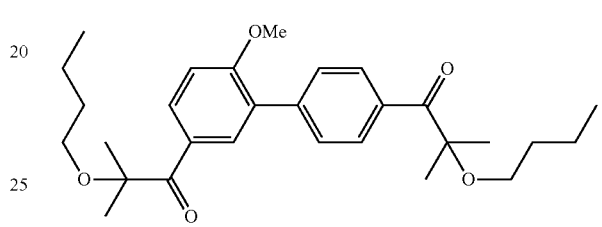
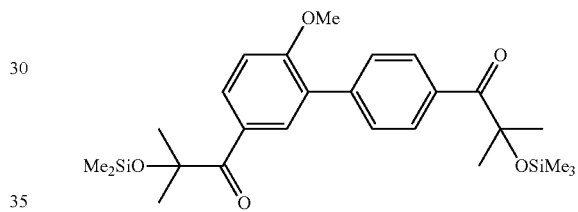
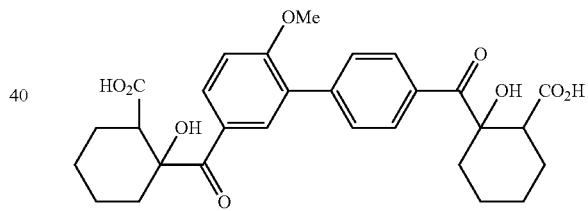
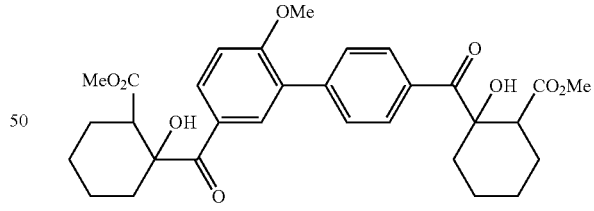
The following specific structures serve as selected but not limiting examples of compounds of formula III (when n=1):
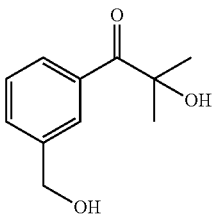
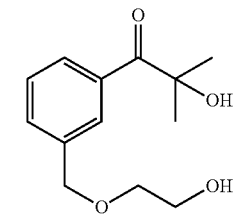

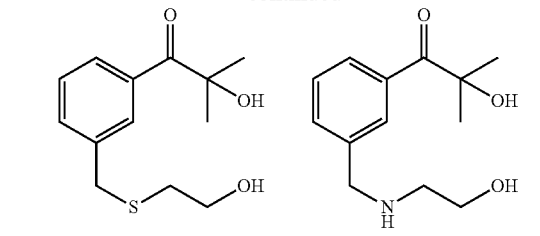
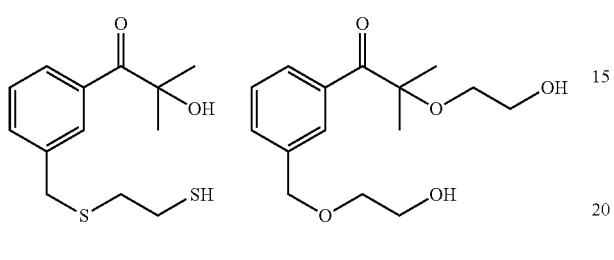
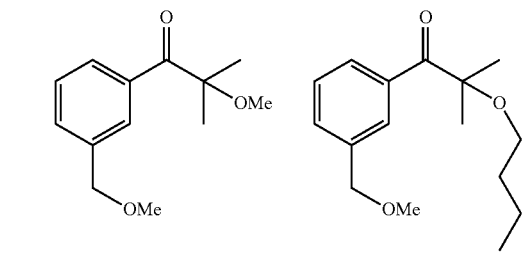
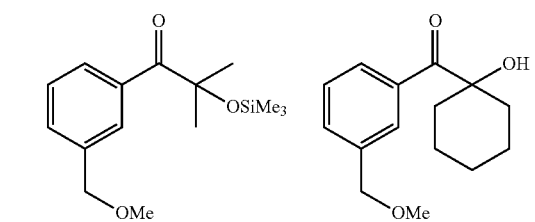
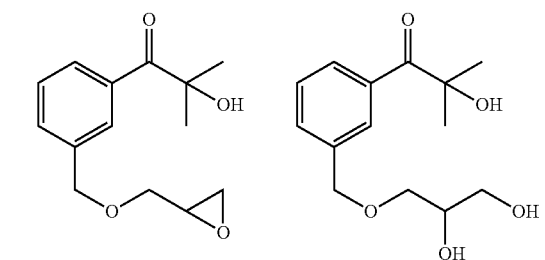
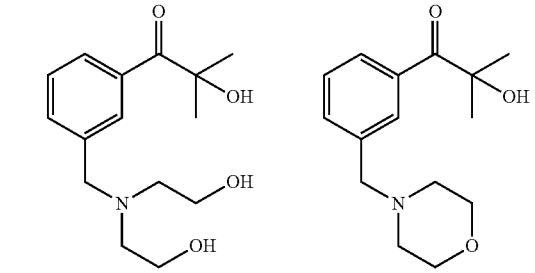
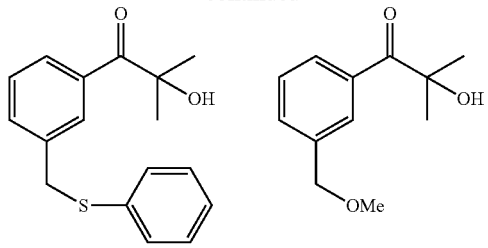
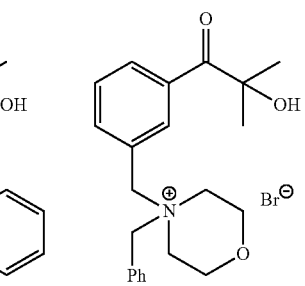
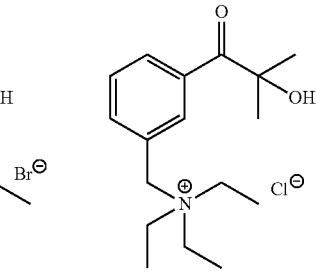
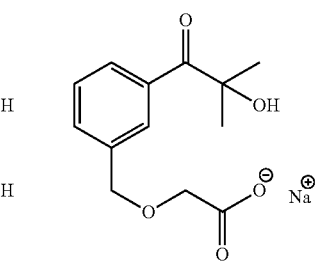
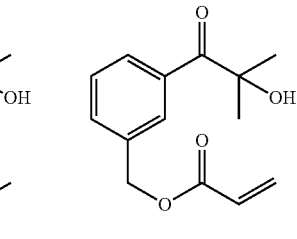
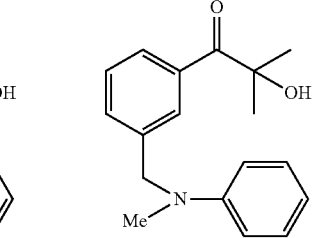

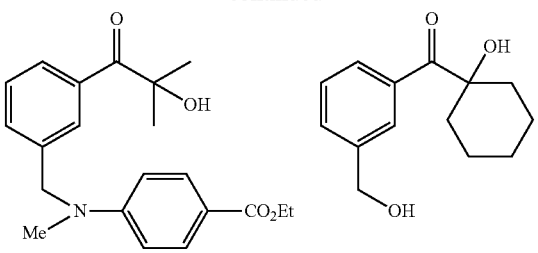
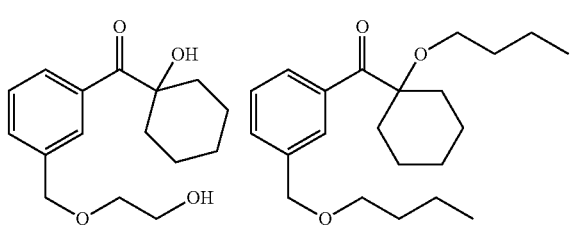
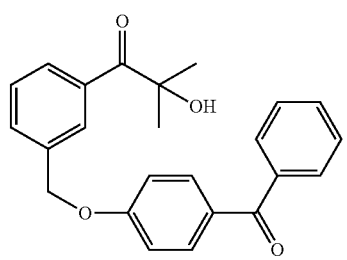
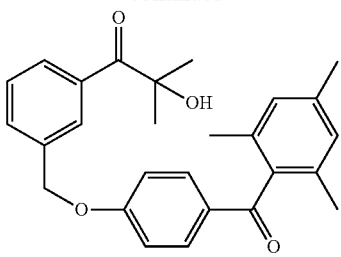
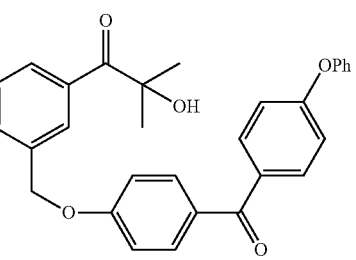
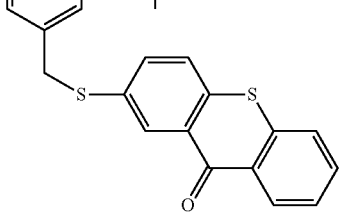
The following specific structures serve as selected but not limiting examples of compounds of formula III (when n=2, 3, 4, 5, or 6):
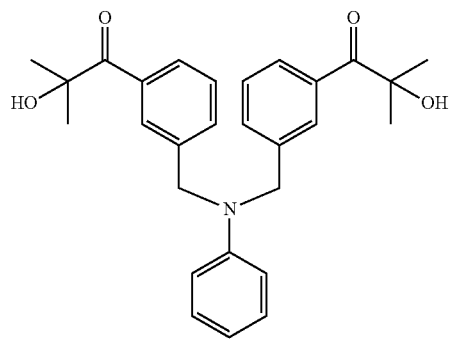
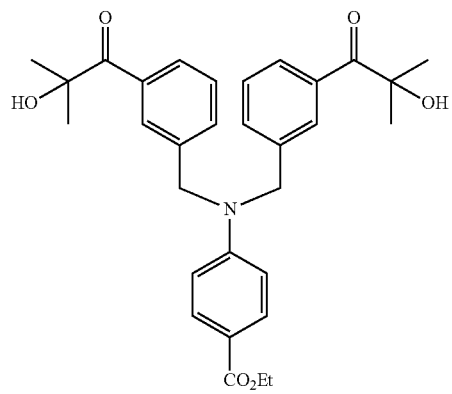
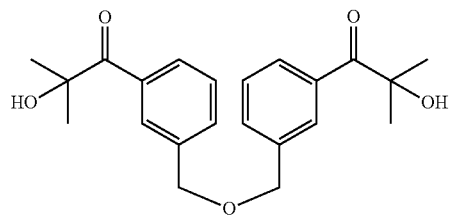
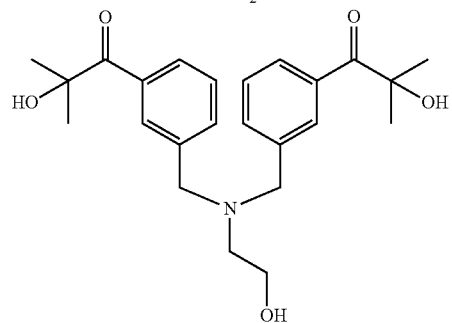

21    -continued    22
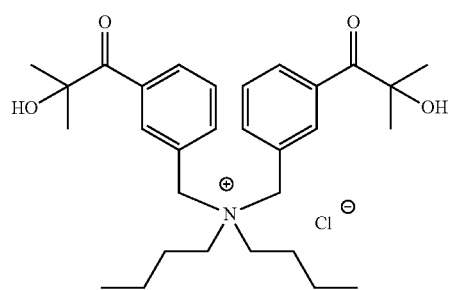
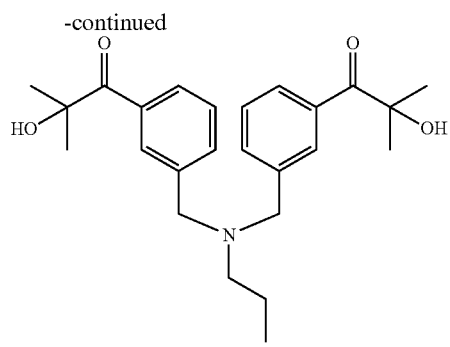
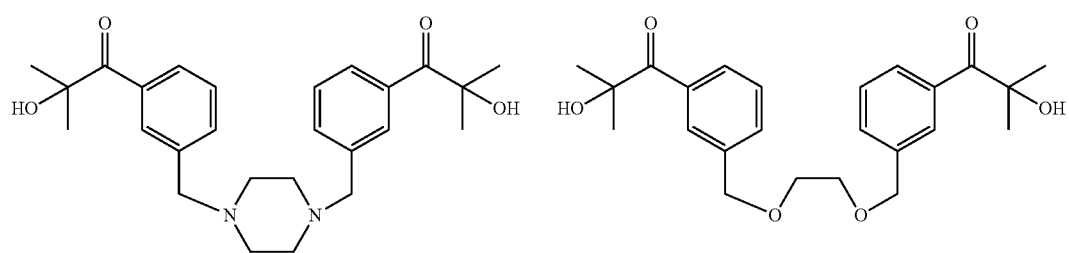
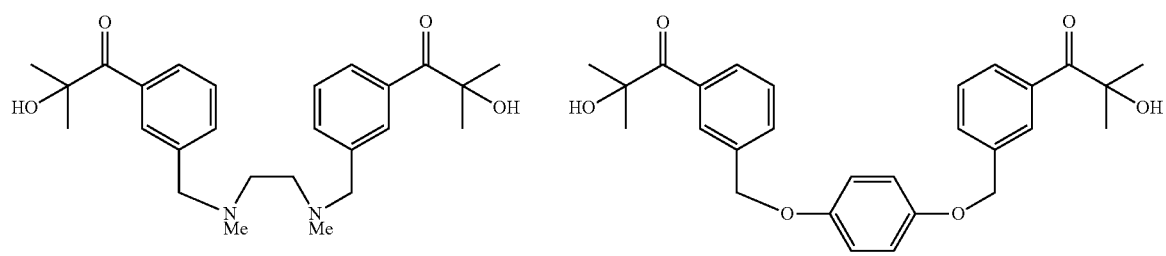
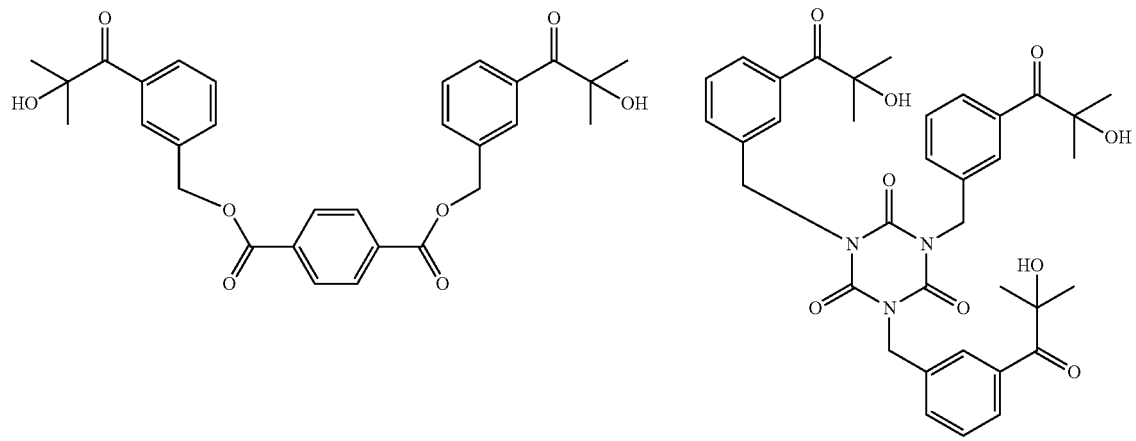
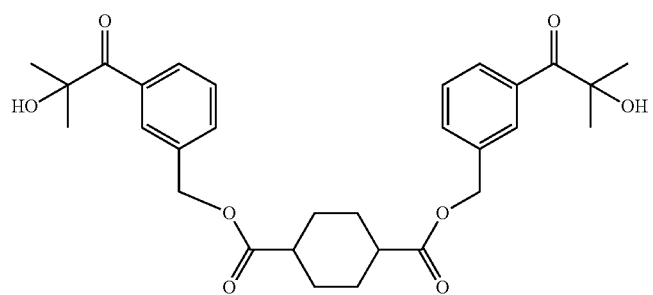

23
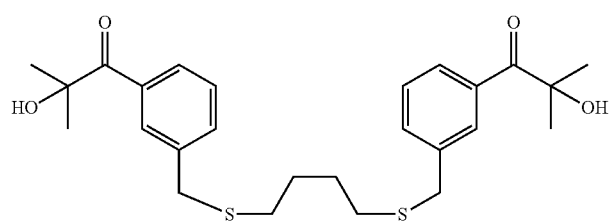
24
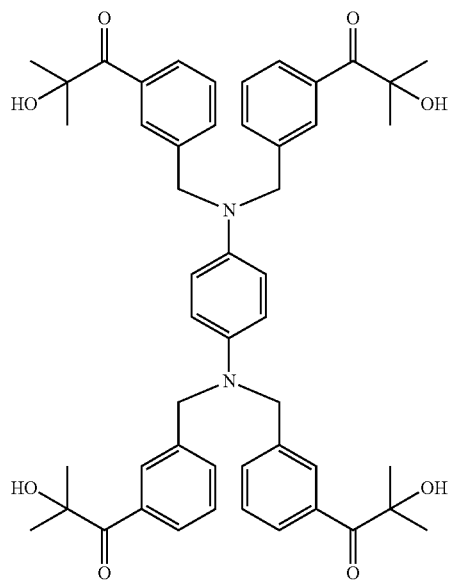
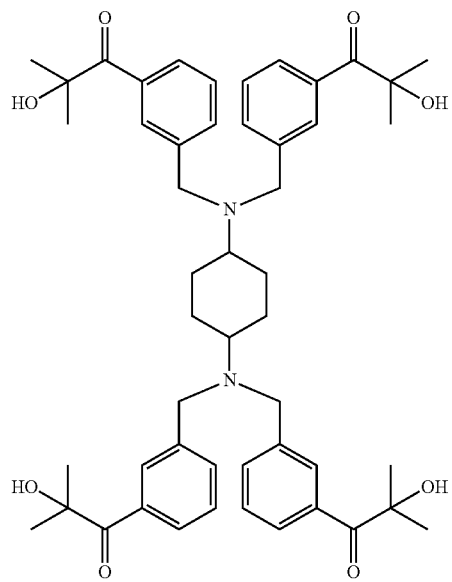
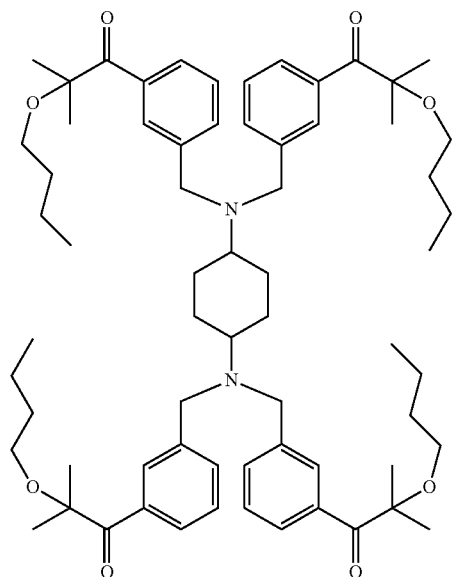
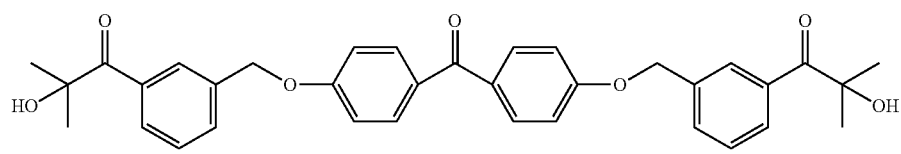
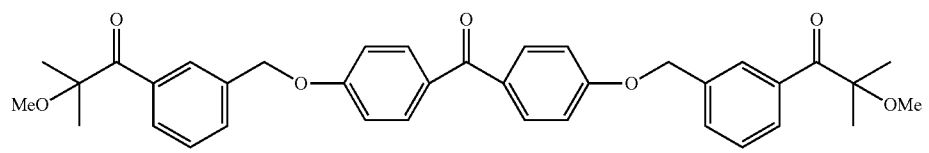

-continued
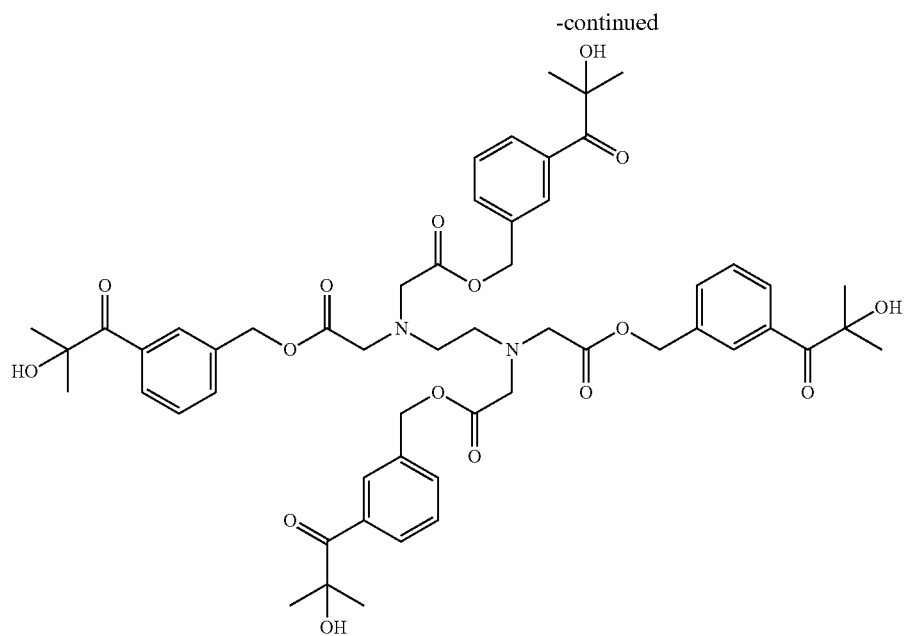
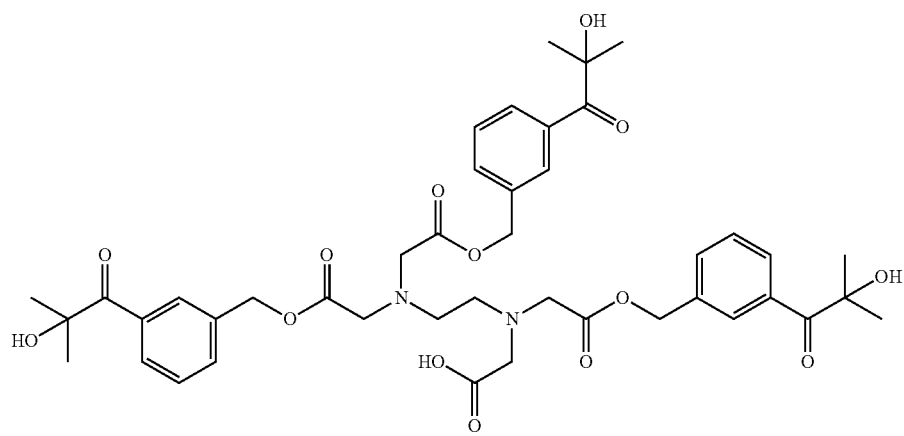
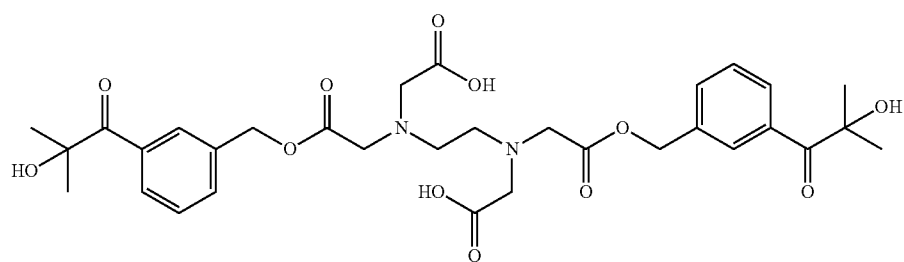

-continued
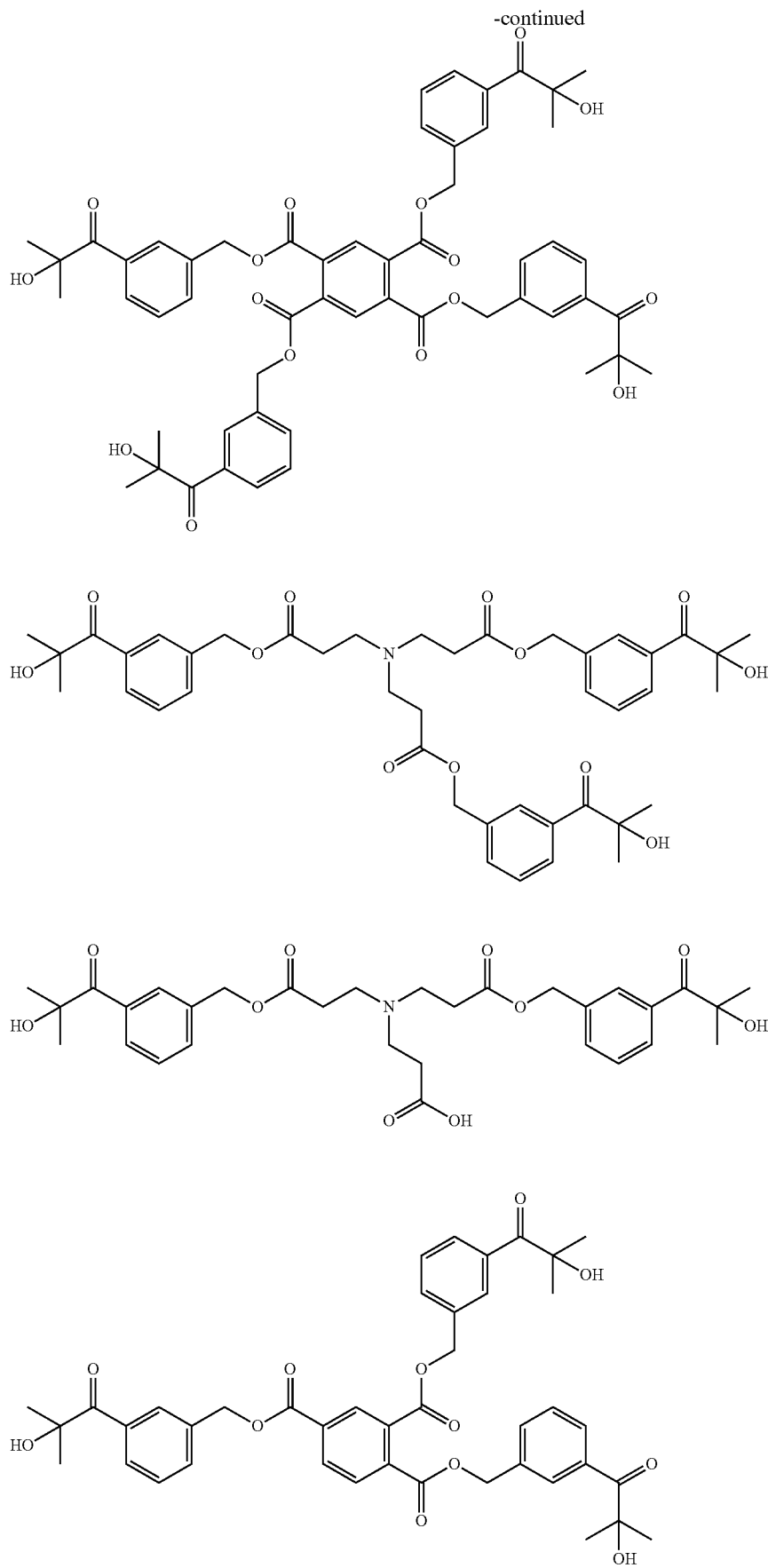

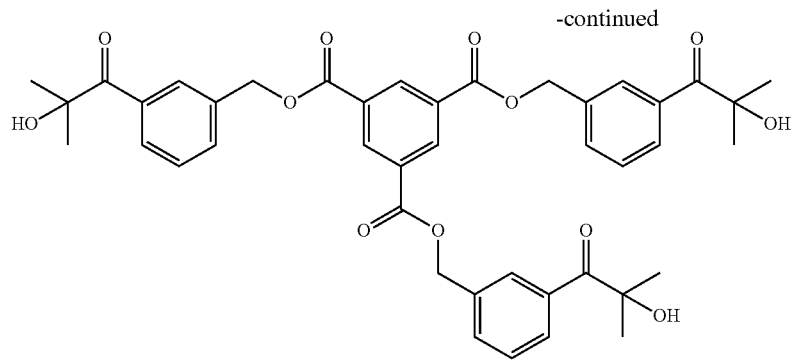

The compounds disclosed in the present invention can be used as photo-initiators or effective components of photo-initiator mixtures for the photopolymerizations of ethylenically unsaturated systems.

The following examples served to illustrate the invention in more details.

EXAMPLE 1

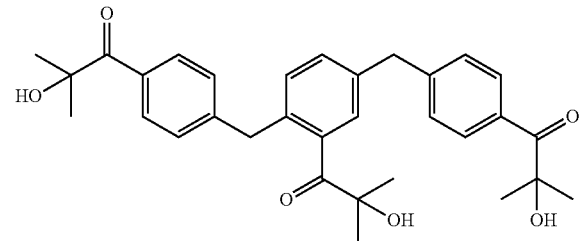 [SMILES: CC(C)(O)C(=O)c1ccc(Cc2ccc(Cc3ccc(C(=O)C(C)(C)O)cc3)c(C(=O)C(C)(C)O)c2)cc1]

Under nitrogen atmosphere 8.4 grams of 1,4-dibenzylbenzene and 11.9 grams isobutyryl chloride were mixed in 400 mL of freshly distilled dichloromethane, followed by portion wise addition of 15.6 grams of anhydrous $AlCl_3$ powder with stirring at room temperature. The mixture was stirred continuously overnight at this temperature and was poured into 1 L of 2N HCl solution. The organic layer was separated and the aqueous layer was extracted twice with 300 mL dichloromethane. The organic layers were combined and washed twice by water and brine, respectively. The concentrated residue was then loaded onto silica gel column and eluted by mixtures of hexane/ethyl acetate to give 10.2 grams of the corresponding tri-acylated aryl ketone intermediate. This intermediate was subsequently dissolved in 300 mL of dichloromethane, to which 10.4 grams of bromine was added dropwise. The reaction progress was monitored by thin-layer chromatography (TLC) and the solvent was removed under vacuo after the reaction completion was detected. The solid residue was next hydrolyzed with 300 mL of 2N NaOH solution. Crude product was purified by means of silica gel chromatography with mixtures of hexane/ethyl acetate as eluents, yielding 5.3 grams of the target product. $^1$H NMR ($CDCl_3$, unit in ppm): 7.99-7.94 (m, 5H), 7.33-7.21 (m, 6H), 4.09 (s, 4H), 4.00 (s, 2H), 3.39 (s, 1H), 1.62 (s, 18H); $^{13}$C NMR ($CDCl_3$, unit in ppm): 204.0, 146.7, 145.4, 140.3, 131.9, 130.3, 130.1, 130.0, 129.7, 129.3, 129.0, 128.9, 127.2, 75.3, 41.7, 41.5, 28.5;

EXAMPLE 2

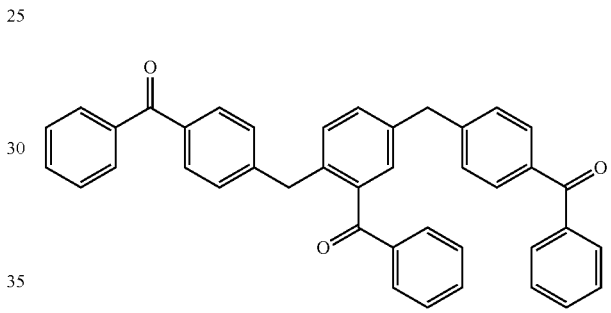

Step one: under nitrogen atmosphere 5.2 grams of 1,4-dibenzylbenzene and 6.8 grams of benzoyl chloride were mixed in 350 mL of freshly distilled dochloromethane, followed by portion wise addition of 6.5 grams of anhydrous $AlCl_3$ powder with stirring at room temperature. The mixture was stirred continuously for 6 hr at this temperature and was poured into 750 mL of 2N HCl solution. The organic layer was separated and the aqueous layer was extracted twice with 300 mL dichloromethane. The organic layers were combined and washed twice by water and brine, respectively. The concentrated residue was then loaded onto silica gel column and eluted by mixtures of hexane/ethyl acetate to give 5.7 grams of the corresponding aryl ketone intermediate. $^1$H NMR ($CDCl_3$, ppm): 7.80-7.18 (m, 12H), 4.04 (s, 4H); $^{13}$C NMR ($CDCl_3$, ppm): 189.2, 129.1, 133.1, 133.0, 130.9, 128.6, 125.1, 124.1, 123.4, 123.0, 122.9, 122.1, 122.0, 121.9, 121.6, 121.4, 121.2, 120.7, 120.3, 119.5, 118.4, 34.9;

Step two: under nitrogen atmosphere 1.5 grams of benzoyl chloride and 1.8 grams of anhydrous $AlC_{13}$ powder were mixed in 200 mL of freshly distilled dichloromethane. After stirring the mixture for 30 mins at room temperature, 5.7 grams of the intermediate prepared in the above step one was added portion wise and the resultant mixture was further stirred for 2 hr. The mixture was then poured into 400 mL of 2N HCl solution. The organic layer was separated and the aqueous layer was extracted twice with dichloromethane of equal volumes. The organic layers were combined and washed twice by water and brine, respectively. The concentrated residue was then loaded onto silica gel column and eluted by mixtures of hexane/ethyl acetate to give 3.3 grams of the target product. C/H elemental analyses: C, 86.29%; H, 5.30% (theoretical); C, 86.63%; H, 5.62% (experimental).

EXAMPLE 3

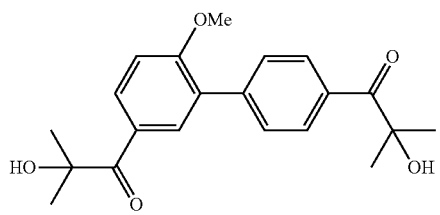 [SMILES: COc1ccc(C(=O)C(C)(C)O)cc1-c1ccc(C(=O)C(C)(C)O)cc1]

Under nitrogen atmosphere 4.3 grams of 1,1'-(6-methoxy-[1,1'-biphenyl]-3,4'-diyl)bis(2-methylpropan-1-one), which was prepared by following a procedure described in the below Example 4 for the synthesis of (6-methoxy-[1,1'-biphenyl]-3,4'-diyl)bis(phenylmethanone), was mixed with 80 mL of dry dichloromethane and 10 mL of $CCl_4$ at room temperature. 4.2 grams of bromine was added and the resultant solution was continuously stirred at this temperature until the reaction completion was detected by TLC monitoring. The mixture was then concentrated and the residue was mixed with 100 mL of 2N NaOH solution. After stirring overnight the mixture was poured into 200 mL of water, and the aqueous layer was extracted by 100 mL of dichloromethane. The combined organic layer was washed by brine and dried over $MgSO_4$. The filtered solution was then concentrated and the residue was loaded onto silica gel column and eluted by mixtures of hexane/ethyl acetate to give 3.6 grams of the light-yellow product (77% yield). $^1$H NMR ($CDCl_3$, ppm): 8.13-8.09 (m, 4H), 7.63 (d, 2H, J=8.4 Hz), 7.05 (d, 1H, J=9.0 Hz), 4.17 (s, 1H), 4.16 (s, 1H), 1.68 (s, 6H), 1.65 (s, 6H); $^{13}$C NMR ($CDCl_3$, ppm): 204.0, 202.4, 160.2, 142.2, 133.0, 132.3, 129.6, 129.5, 129.2, 126.1, 110.6, 77.4, 76.0, 55.8, 28.6, 28.1.

EXAMPLE 4

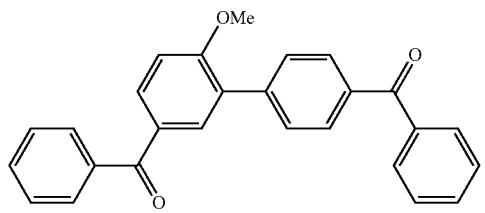 [SMILES: COc1ccc(C(=O)c2ccccc2)cc1-c1ccc(C(=O)c2ccccc2)cc1]

Step one: under nitrogen atmosphere 11 grams of anhydrous $AlCl_3$ powder was suspended in 50 mL of dry dichloromethane. 12 grams of benzoyl chloride was added at room temperature and the resultant solution was next combined with 16 grams of 2-methoxy-1,1'-biphenyl in 60 mL of dichloromethane. The mixture was stirred for 2 hrs at room temperature and poured into 200 mL of ice-cold 1N HCl solution to give a clear solution of two payers. The organic layer was separated and dried over anhydrous $MgSO_4$. The filtered solution was then concentrated and the residue was used in the next step experiment without further purification.

Step two: under nitrogen atmosphere 12 grams of anhydrous $AlCl_{13}$ powder was suspended in 50 mL of dry dichloromethane, to which 13 grams of benzoyl chloride was added slowly to give a clear solution with stirring at room temperature. The above obtained intermediate in 50 mL of $CS_2$ was then added and the resultant mixture was stirred at 45-55° C. for 5 hrs. The mixture was poured into 200 mL of 2N HCl solution. The organic layer was separated and dried over anhydrous $MgSO_4$. The filtered solution was concentrated and the residue was then loaded onto silica gel column and eluted by mixtures of hexane/ethyl acetate to give the target product as light-yellow wax (72% yield over two steps). $^1$H NMR ($CDCl_3$, ppm): 7.91-7.72 (m, 8H), 7.67-7.45 (m, 8H), 7.09 (d, 1H), 3.92 (s, 3H); $^{13}$C NMR ($CDCl_3$, ppm): 196.3, 195.4, 160.1, 141.8, 138.1, 137.8, 136.4, 133.1, 132.5, 132.1, 130.4, 130.0, 129.8, 129.5, 128.3, 110.7, 55.9.

EXAMPLE 5

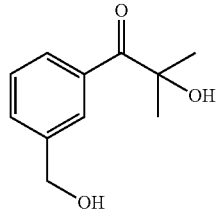

Step one: under nitrogen atmosphere 5 grams of Darocur 1173 (2-hydroxy-2-methyl-1-phenylpropan-1-one) was mixed with 24 grams of anhydrous $AlCl_3$ in 100 mL of dry chloroform. Upon cooling to 4° C. 4.5 grams of paraformaldehyde powder was slowly added and the resultant mixture was stirred at room temperature for 12 hrs (note that HCl gas released from the reaction was neutralized by 2N NaOH solution). The mixture was poured into water, and the precipitate generated was dissolved by adding 2N HCl solution. The organic layer thus separated was collected, and the aqueous layer was extracted with ethyl acetate for three times. The combined chloroform and ethyl acetate layer was next dried over anhydrous $Na_2SO_4$, filtered, and concentrated. The residue was loaded onto silica gel column and eluted by mixtures of hexane/ethyl acetate (V/V=15/1) to give the intermediate 1-(3-(chloromethyl)phenyl)-2-hydroxy-2-methylpropan-1-one as a light-yellow oil (33% yield).

Step two: under nitrogen atmosphere 25 grams of the intermediate 1-(3-(chloromethyl)phenyl)-2-hydroxy-2-methylpropan-1-one was mixed with 9.4 grams of NaOH in 300 mL of water. The mixture was refluxed for 12 hrs, cooled to room temperature, and extracted with 400 mL of ethyl acetate for three times. The organic layer was dried over $Na_2SO_4$, concentrated, and the residue was loaded onto silica gel column and eluted by mixtures of hexane/ethyl acetate (V/V=5/1) to give the target product as a light-yellow oil (38% yield) which solidified upon standing.

Step two (a modified procedure): under nitrogen atmosphere and at 40° C. 25 grams of the intermediate 1-(3-(chloromethyl)phenyl)-2-hydroxy-2-methylpropan-1-one was mixed with 1.2 eq of LiOH (0.5N solution) and further stirred overnight. The mixture was neutralized by 2N HCl and then extracted three times with ethyl acetate of equal volume. The combined organic layer was dried over $Na_2SO_4$, concentrated, and the residue was loaded onto silica gel column and eluted by mixtures of hexane/ethyl acetate (V/V=5/1) to give the target product as a light-yellow oil (92% yield) which solidified as white crystals upon standing. $^1$H NMR ($CDCl_3$, ppm): 7.89 (s, 1H), 7.82 (d, 1H, J=7.8 Hz), 7.39 (d, 1H, J=7.5 Hz), 7.29 (dd, J=7.8 Hz, J=7.5 Hz, 1H), 4.52 (s, 2H), 4.17 (s, 1H), 1.47 (s, 6H); $^{13}$C NMR ($CDCl_3$, ppm): 204.9, 141.3, 134.2, 131.2, 128.6, 128.3, 127.9, 76.8, 64.0, 28.1.

EXAMPLE 6

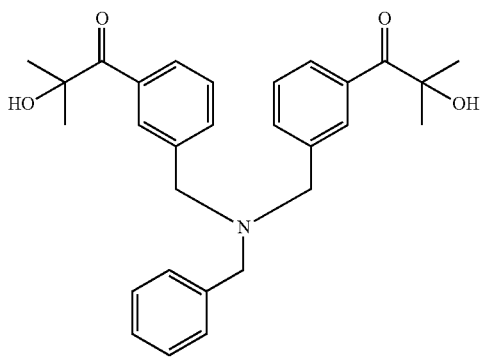 [SMILES: CC(C)(O)C(=O)c1cccc(CN(Cc2ccccc2)Cc2cccc(C(=O)C(C)(C)O)c2)c1]

Under nitrogen atmosphere 0.84 grams of 1-(3-(chloromethyl)phenyl)-2-hydroxy-2-methylpropan-1-one was mixed with 0.84 grams of phenylmethanamine and 2 grams of $NaHCO_3$ in 100 mL of water, the mixture was refluxed for 12 hrs, cooled to room temperature, and extracted three times with 200 mL of ethyl acetate. The combined organic layer was dried over $Na_2SO_4$, concentrated, and the residue was loaded onto silica gel column and eluted by mixtures of hexane/ethyl acetate (V/V=4/1) to give the target product as a light-yellow oil (80% yield). $^1$H NMR ($CDCl_3$, ppm): 8.12 (s, 2H), 7.91 (d, 2H, J=7.7 Hz), 7.59 (d, 2H, J=7.6 Hz), 7.46-7.22 (m, 7H), 4.22 (s, 2H), 3.64 (s, 4H), 3.61 (s, 2H), 1.64 (s, 12H); $^{13}$C NMR ($CDCl_3$, ppm): 204.8, 139.9, 138.9, 133.9, 133.2, 130.0, 128.8, 128.5, 128.4, 128.3, 127.2, 76.5, 58.2, 57.7, 28.5.

EXAMPLE 7

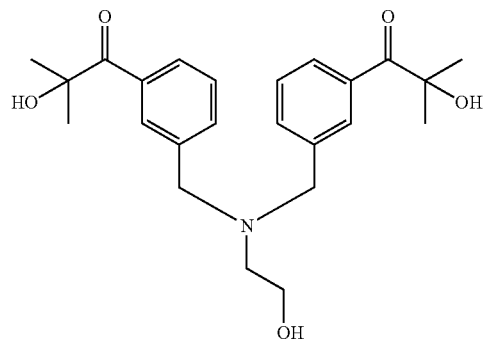 [SMILES: CC(C)(O)C(=O)c1cccc(CN(CCO)Cc2cccc(C(=O)C(C)(C)O)c2)c1]

Under nitrogen atmosphere 13 grams of 1-(3-(chloromethyl)phenyl)-2-hydroxy-2-methylpropan-1-one was mixed with 1.5 mL of 2-aminoethanol and 5.2 grams of $NaHCO_3$ in 250 mL of water, the mixture was refluxed for 12 hrs, cooled to room temperature, and extracted three times with 400 mL of ethyl acetate. The combined organic layer was dried over $Na_2SO_4$, concentrated, and the residue was loaded onto silica gel column and eluted by mixtures of hexane/ethyl acetate (V/V=3/1) to give the target product as a light-yellow oil (90% yield). $^1$H NMR ($CDCl_3$, ppm): 8.04 (s, 2H), 7.87 (d, 2H, J=7.8 Hz), 7.47 (d, 2H, J=7.5 Hz), 7.36 (dd, 2H, J=7.8 Hz, J=7.5 Hz), 4.30 (s, 2H), 3.65 (s, 4H), 3.56 (t, 2H, J=5.4 Hz), 2.65 (s, 1H), 2.64 (t, 2H, J=5.4 Hz), 1.56 (s, 12H); $^{13}$C NMR ($CDCl_3$, ppm): 204.5, 139.1, 134.1, 133.0, 130.1, 128.5, 128.3, 76.6, 58.9, 58.1, 55.2, 28.2.

EXAMPLE 8

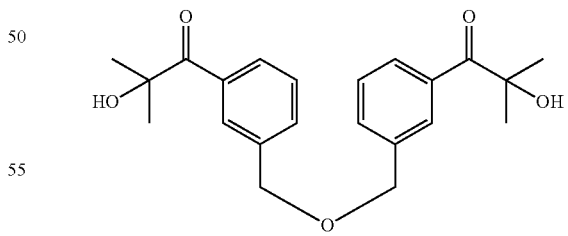

This target product was isolated from the step two of Example 5 in the form of colorless oil and with 51% yield. $^1$H NMR ($CDCl_3$, ppm): 8.01 (s, 2H), 7.93 (d, 2H, J=7.8 Hz), 7.52 (d, 2H, J=7.5 Hz), 7.38 (dd, J=7.8 Hz, J=7.5 Hz, 2H), 4.58 (s, 4H), 4.22 (s, 2H), 1.55 (s, 12H); $^{13}$C NMR ($CDCl_3$, ppm): 204.6, 138.4, 134.2, 132.0, 129.1, 128.9, 128.5, 76.7, 71.8, 28.3.

EXAMPLE 9

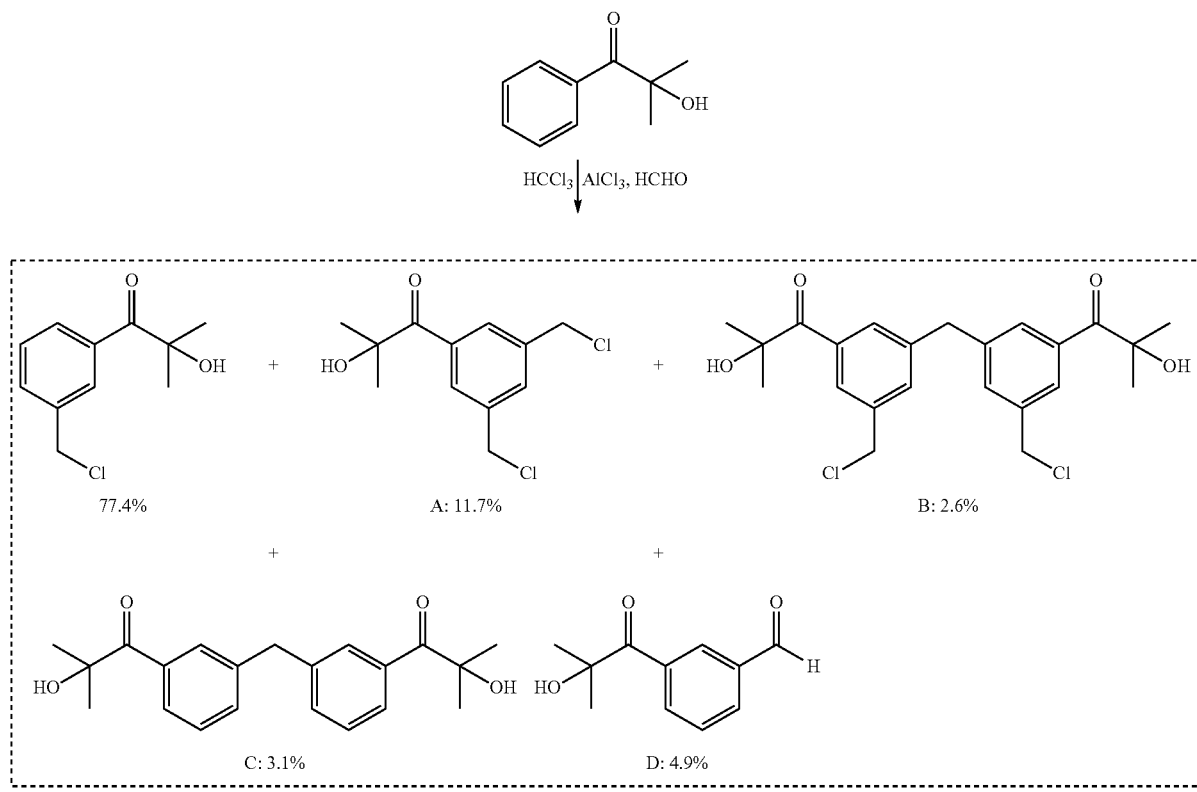

Under nitrogen atmosphere 100 grams of Darocur 1173 (2-hydroxy-2-methyl-1-phenylpropan-1-one) was placed in 2 L of dry chloroform. After the mixture was cooled to 0° C., 480 grams of anhydrous $AlCl_3$ and 55 grams of paraformaldehyde powder were successively added and the resultant mixture was vigorously stirred at 60° C. overnight for 14 hrs (note that HCl gas released from the reaction was neutralized by 2N NaOH solution). An additional portion of 55 grams of paraformaldehyde was added at this point and the reaction was stirred at this temperature for another 12 hrs. The mixture was cooled to room temperature, and under vigorous stirring poured into 3 L of water. The organic layer thus separated was collected, and the aqueous layer was extracted with 1 L of dichloromethane for three times. The combined chloroform and dichloromethane layer was next dried over anhydrous $Na_2SO_4$, filtered, and concentrated. The residue was loaded onto silica gel column and gradient eluted by mixtures of hexane/ethyl acetate (V/V=15/1 to 12/1) to give the intermediate 1-(3-(chloromethyl)phenyl)-2-hydroxy-2-methylpropan-1-one as a light-yellow oil (77.4% yield), and four other by-products A-D (22.6% combined yield). Characterization data for compound A (11.7% yield): $^1$H NMR ($CDCl_3$, ppm): 8.01 (s, 2H), 7.63 (s, 1H), 4.63 (s, 4H), 3.78 (s, 1H), 1.62 (s, 6H); $^{13}$C NMR ($CDCl_3$, ppm): 203.7, 138.5, 135.0, 132.7, 129.7, 76.7, 45.2, 28.3; Compound B (2.6% yield): $^1$H NMR ($CDCl_3$, ppm): 7.93 (s, 2H), 7.82 (s, 2H), 7.43 (s, 2H), 4.60 (s, 4H), 4.12 (s, 2H), 3.82 (s, 2H), 1.59 (s, 12H); Compound C (3.1% yield): $^1$H NMR ($CDCl_3$, ppm): 7.89 (dd, 2H), 7.86 (s, 2H), 7.42-7.40 (m, 4H), 4.10 (s, 2H), 4.05 (s, 2H), 1.60 (s, 12H); $^{13}$C NMR ($CDCl_3$, ppm): 204.7, 140.8, 134.2, 133.4, 130.1, 128.7, 127.8, 76.5, 41.5, 28.4; Compound D (4.9% yield): $^1$H NMR ($CDCl_3$, ppm): 10.06 (s, 1H), 8.54 (s, 1H), 8.31 (d, 1H, J=7.5 Hz), 8.06 (d, 1H, J=7.6 Hz), 7.62 (dd, 1H, J=7.5 Hz, J=7.6 Hz), 3.89 (s, 1H), 1.61 (s, 6H); $^{13}$C NMR ($CDCl_3$, ppm): 203.4, 191.9, 136.0, 135.5, 135.3, 132.6, 131.5, 128.9, 77.0, 27.9.

EXAMPLE 10

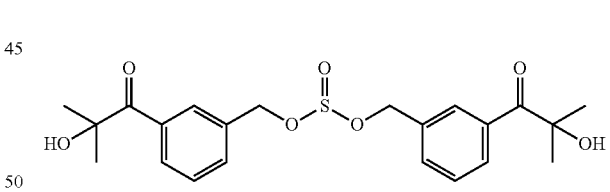

Under nitrogen atmosphere and at 0° C. 1.8 mL of $SOCl_2$ was diluted with 2 mL of dichloromethane and then added dropwise into 3 mL dichloromethane solution containing 0.58 grams of 2-hydroxy-1-(3-(hydroxymethyl)phenyl)-2-methylpropan-1-one (Example 5) and 0.55 mL of $Et_3N$. The mixture was stirred for 3 hrs and poured into 20 mL of water, and further extracted three times with ethyl acetate of equal volume. The combined organic layer was washed by water and saturated $NaHCO_3$ successively, dried over $Na_2SO_4$, filtered, and concentrated. The residue was loaded onto silica gel column and gradient eluted by mixtures of hexane/ethyl acetate (V/V=1/1) to give the target product as colorless oil (92% yield). $^1$H NMR ($CDCl_3$, ppm): 8.00 (2H, d, J=7.7 Hz), 7.98 (s, 2H), 7.53 (d, 2H, J=7.6 Hz), 7.44 (dd, 2H, J=7.7 Hz, J=7.6 Hz), 5.09 (d, 2H, J=12.1 Hz), 4.98 (d, 2H, J=12.1 Hz), 3.84 (s, 2H), 1.60 (s, 12H); $^{13}$C NMR (CDCl$_3$, ppm): 204.3, 135.6, 134.5, 132.6, 129.8, 129.6, 128.8, 76.7, 63.6, 28.3; High resolution mass spectrometry: C$_{22}$H$_{27}$O$_7$S (M+H), 435.1477 (theoretical); 435.1442 (experimental).

EXAMPLE 11

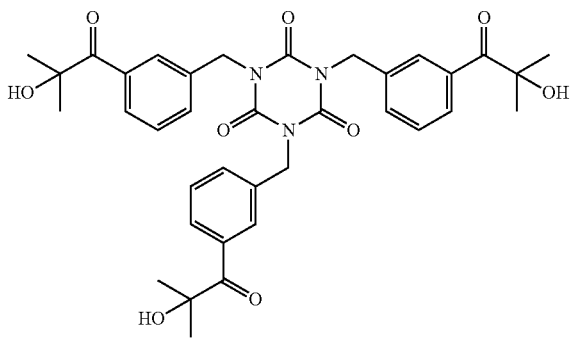 [SMILES: CC(C)(O)C(=O)c1cccc(Cn2c(=O)n(Cc3cccc(C(=O)C(C)(C)O)c3)c(=O)n(Cc3cccc(C(=O)C(C)(C)O)c3)c2=O)c1]

To a round-bottom flask containing 55 mL of DMF was added successively 5.1 grams of 1-(3-(chloromethyl)phenyl)-2-hydroxy-2-methylpropan-1-one, 0.95 grams of 1,3,5-triazinane-2,4,6-trione, and 3.3 grams of K$_2$CO$_3$ powder. The mixture was refluxed for 16 hrs and cooled to room temperature, to which 200 mL of water was added. The mixture was extracted by 100 mL each of ethyl acetate for three times, and the combined organic layer was washed by brine for three times and then dried over 8 grams of anhydrous Na$_2$CO$_3$. The organic layer was filtered, concentrated, and the residue was loaded onto silica gel column and eluted by mixtures of hexane/ethyl acetate (V/V=5/1) to give the target product as colorless solid (64% yield). $^1$H NMR (CDCl$_3$, ppm): 8.15 (s, 3H), 7.95 (d, 3H, J=7.6 Hz), 7.67 (d, 3H, J=7.2 Hz), 7.43 (dd, 3H, J=7.6 Hz, J=7.2 Hz), 5.09 (s, 6H), 3.98 (s, 3H), 1.60 (s, 18H); $^{13}$C NMR (CDCl$_3$, ppm): 204.1, 148.9, 135.7, 134.4, 133.3, 130.3, 129.4, 128.6, 76.6, 45.9, 28.2.

EXAMPLE 12

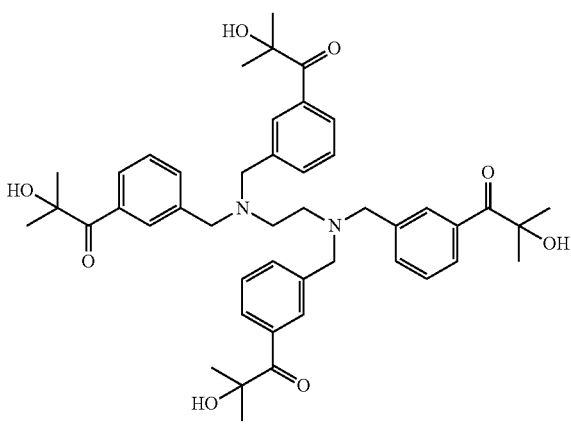 [SMILES: CC(C)(O)C(=O)c1cccc(CN(CCN(Cc2cccc(C(=O)C(C)(C)O)c2)Cc2cccc(C(=O)C(C)(C)O)c2)Cc2cccc(C(=O)C(C)(C)O)c2)c1]

To a round-bottom flask containing 0.6 grams of ethane-1,2-diamine, 20 mL of water, and 1.2 grams of NaOH was added dropwise a solution of 10.6 grams of 1-(3-(chloromethyl)phenyl)-2-hydroxy-2-methylpropan-1-one in 20 mL of toluene. The resultant mixture was next refluxed for 11 hrs and cooled to room temperature. The organic layer was separated, and the aqueous layer was extracted by 40 mL of ethyl acetate for three times. The combined organic layer was washed by brine for three times and then dried over anhydrous Na$_2$SO$_4$. The organic layer was filtered, concentrated, and the residue was loaded onto silica gel column and eluted by mixtures of hexane/ethyl acetate (V/V=4/1) to give the target product as colorless oil (33% yield). $^1$H NMR (CDCl$_3$, ppm): 7.98 (s, 4H), 7.86 (d, 4H, J=8.0 Hz), 7.46 (d, 4H, J=7.6 Hz), 7.34 (dd, 4H, J=8.0 Hz, J=7.6 Hz), 4.16 (s, 4H), 3.57 (s, 8H), 2.65 (s, 4H), 1.56 (s, 24H); $^{13}$C NMR (CDCl$_3$, ppm): 204.7, 139.8, 133.9, 133.1, 129.9, 128.5, 128.3, 76.6, 58.4, 51.6, 28.4.

EXAMPLE 13

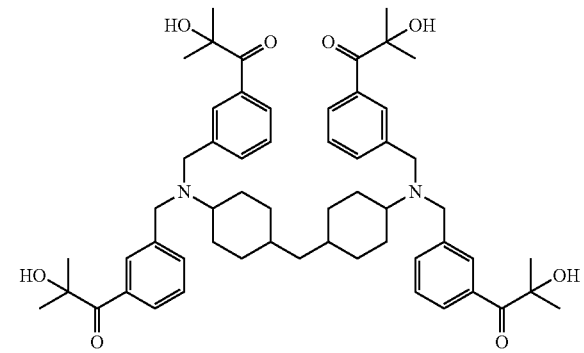 [SMILES: CC(C)(O)C(=O)c1cccc(CN(Cc2cccc(C(=O)C(C)(C)O)c2)C2CCC(CC3CCC(N(Cc4cccc(C(=O)C(C)(C)O)c4)Cc4cccc(C(=O)C(C)(C)O)c4)CC3)CC2)c1]

To a round-bottom flask containing 2.1 grams of 4,4'-methylenedicyclo-hexanamine, 20 mL of water, and 1.6 grams of NaOH was added dropwise a solution of 10.6 grams of 1-(3-(chloromethyl)phenyl)-2-hydroxy-2-methylpropan-1-one in 30 mL of toluene. The resultant mixture was next refluxed for 15 hrs and cooled to room temperature. The organic layer was separated, and the aqueous layer was extracted by 40 mL of ethyl acetate for three times. The combined organic layer was washed by brine for three times and then dried over anhydrous Na$_2$SO$_4$. The organic layer was filtered, concentrated, and the residue was loaded onto silica gel column and eluted by mixtures of hexane/ethyl acetate (V/V=4/1) to give 1.4 grams of the target product as colorless oil (16% yield). $^1$H NMR (CDCl$_3$, ppm): 8.02 (s, 4H), 7.83 (d, 4H, J=8.0 Hz), 7.53 (d, 4H, J=7.2 Hz), 7.33 (dd, 4H, J=8.0 Hz, J=7.2 Hz), 4.37 (s, 4H), 3.71 (s, 8H), 2.48 (s, 2H), 1.59 (s, 24H), 1.92-1.17 (m, 18H), 0.99-0.78 (m, 4H); $^{13}$C NMR (CDCl$_3$, ppm): 204.8, 141.3, 141.2, 133.7, 132.9, 129.7, 128.2, 76.4, 58.9, 53.9, 35.1, 34.6, 32.7, 28.4, 21.0.

EXAMPLE 14

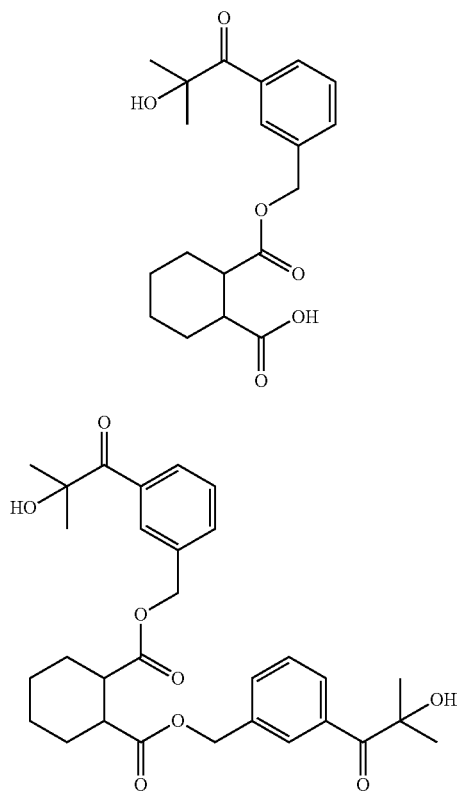

Under nitrogen atmosphere and at room temperature 154.2 mg of hexahydroisobenzofuran-1,3-dione was mixed with 194 mg of 2-hydroxy-1-(3-(hydroxymethyl)phenyl)-2-methylpropan-1-one, 5 mg of N,N-dimethylpyridin-4-amine, and 0.12 mL of Et$_3$N in 2 mL of dry dichloromethane. The mixture was stirred for 2 hrs and diluted by 15 mL of Et$_2$O. The organic layer was washed by saturated NaHCO$_3$ of equal volume. The separated aqueous layer was acidified to pH=2 and extracted twice by ethyl acetate. The combined ethyl acetate layer was concentrated and thus obtained residue was loaded onto silica gel column and eluted by mixtures of hexane/ethyl acetate (V/V=1/1) to give the target product A as colorless oil (94% yield). $^1$H NMR (CDCl$_3$, ppm): 8.02 (s, 1H), 7.94 (d, 1H, J=7.6 Hz), 7.52 (d, 1H, J=7.2 Hz), 7.45 (dd, 1H, J=7.6 Hz, J=7.2 Hz), 5.18 (s, 2H), 2.90 (br, 2H), 1.63 (s, 6H), 2.08-1.95 (m, 2H), 1.84-1.44 (m, 8H); $^{13}$C NMR (CDCl$_3$, ppm): 204.5, 179.2, 173.4, 136.4, 134.4, 132.2, 129.3, 129.1, 128.6, 76.8, 65.7, 42.5, 42.4, 28.2, 26.2, 26.0, 23.7, 23.6.

Under nitrogen atmosphere and at 0° C. 200 mg of compound A as prepared in the immediately above step was mixed with 100 mg of 2-hydroxy-1-(3-(hydroxymethyl)phenyl)-2-methylpropan-1-one, 10 mg of N,N-dimethylpyridin-4-amine, and 0.3 mL of Et$_3$N in 3 mL of dry dichloromethane. The mixture was stirred for 3 hrs and gradually warmed to room temperature and then poured into 10 mL of water. The mixture was extracted by ethyl acetate of equal volume for three times and the combined organic layer was washed with saturated NaHCO$_3$ and saturated NH$_4$Cl. The concentrated oil was loaded onto silica gel column and eluted by mixtures of hexane/ethyl acetate (V/V=2/1) to give the target product B as colorless oil (87% yield). $^1$H NMR (CDCl$_3$, ppm): 7.98 (s, 2H), 7.96 (d, 2H, J=7.6 Hz), 7.51 (d, 2H, J=7.6 Hz), 7.44 (t, 2H, J=7.6 Hz), 5.11 (s, 4H), 4.02 (s, 2H), 2.94 (br, 2H), 1.63 (s, 12H), 2.15-1.44 (m, 8H); $^{13}$C NMR (CDCl$_3$, ppm): 204.5, 173.3, 136.5, 134.2, 132.3, 129.3, 129.1, 128.6, 76.5, 65.6, 42.6, 28.3, 26.4, 23.2.

EXAMPLE 15

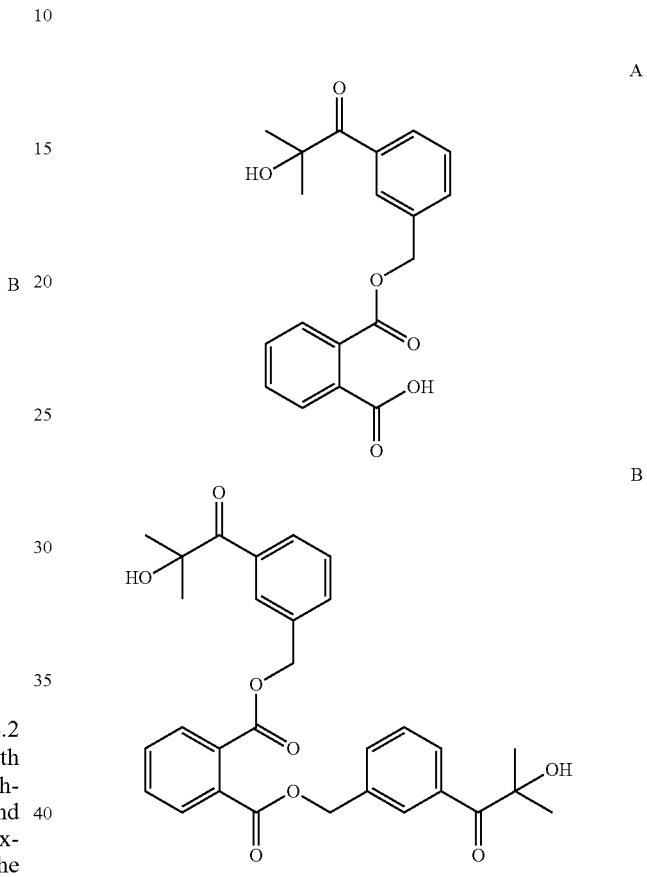

Following procedure similar to that already described for the preparation of compound A in Example 14, the compound A herein was synthesized in 91% isolated yield from the reaction of 148 mg of isobenzofuran-1,3-dione, 194 mg of 2-hydroxy-1-(3-(hydroxymethyl)phenyl)-2-methylpropan-1-one, 5 mg of N,N-dimethylpyridin-4-amine and 0.11 mL of Et$_3$N. $^1$H NMR (CDCl$_3$, ppm): 8.12 (s, 1H), 7.91 (d, 1H, J=7.7 Hz), 7.84 (d, 1H, J=7.1 Hz), 7.71 (d, 1H, J=7.4 Hz), 7.61-7.52 (m, 3H), 7.41 (dd, 1H, J=7.7 Hz, J=7.4 Hz), 5.37 (s, 2H), 1.59 (s, 6H); $^{13}$C NMR (CDCl$_3$, ppm): 204.5, 171.1, 167.9, 135.7, 134.6, 132.7, 132.5, 131.9, 131.1, 130.5, 129.6, 129.5, 128.9, 128.7, 76.8, 67.2, 28.1.

Following procedure similar to that already described for the preparation of compound B in Example 14, the compound B herein was synthesized in 82% isolated yield from the reaction of 172 mg of 2-(((3-(2-hydroxy-2-methylpropanoyl)benzyl)oxy)carbonyl)benzoic acid that is prepared above, 105 mg of 2-hydroxy-1-(3-(hydroxymethyl)phenyl)-2-methylpropan-1-one, 10 mg of N,N-dimethylpyridin-4-amine and 0.12 mL of Et$_3$N. $^1$H NMR (CDCl$_3$, ppm): 8.04 (s, 2H), 7.97 (d, 2H, J=7.9 Hz), 7.73 (m, 2H), 7.54 (m, 2H), 7.44 (dd, 2H), 5.27 (s, 4H), 3.99 (br, 2H), 1.58 (s, 12H); $^{13}$C NMR (CDCl$_3$, ppm): 204.2, 167.2, 135.9, 134.5, 132.5, 131.7, 131.4, 129.6, 129.5, 129.1, 128.6, 127.9, 126.0, 125.9, 76.7, 66.9, 28.3.

EXAMPLE 16

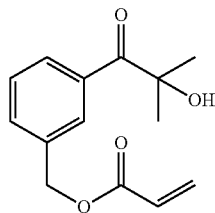 [SMILES: C=CC(=O)OCc1cccc(C(=O)C(C)(C)O)c1]

Under nitrogen atmosphere and at 0° C., 194 mg of 2-hydroxy-1-(3-(hydroxymethyl)phenyl)-2-methylpropan-1-one was dissolved in 2 mL of dichloromethane, to which was added 99 mg of acryloyl chloride in 1 mL of dichloromethane, 0.15 mL of Et$_3$N, and 5 mg of N,N-dimethylpyridin-4-amine. The mixture was stirred for 2 hrs and gradually warmed to room temperature. The mixture was poured into 10 mL of water and extracted twice with ethyl acetate of equal volume. The combined organic layer was washed by brine, dried, filtered, and concentrated to give a crude oil which was further purified by silica gel column chromatography with mixtures of hexane/ethyl acetate (V/V=2/1) to give the target product as colorless oil (91% yield). $^1$H NMR (CDCl$_3$, ppm): 8.05 (s, 1H), 7.99 (d, 1H, J=7.6 Hz), 7.57 (d, 1H, J=7.6 Hz), 7.46 (t, 1H, J=7.6 Hz), 6.45 (d, 1H, J=17.2 Hz), 6.16 (dd, 1H, J=17.2 Hz, J=10.1 Hz), 5.87 (d, 1H, J=10.1 Hz), 5.24 (s, 2H), 4.08 (br, 1H), 1.62 (s, 6H); $^{13}$C NMR (CDCl$_3$, ppm): 204.3, 165.9, 136.4, 134.2, 132.4, 131.3, 129.5, 128.9, 127.8, 125.7, 76.5, 65.7, 28.3.

EXAMPLE 17

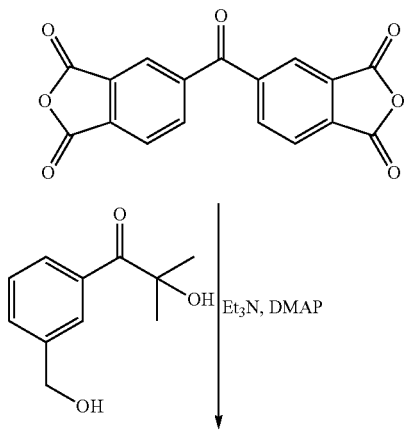

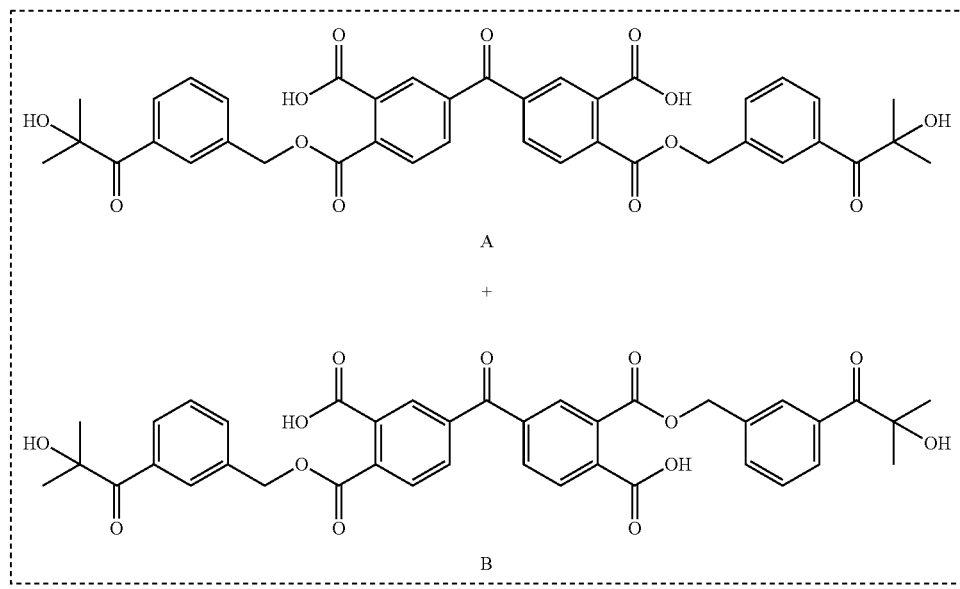

Under nitrogen atmosphere 322 mg of 5,5'-carbonylbis(isobenzofuran-1,3-dione) and 388 mg of 2-hydroxy-1-(3-(hydroxymethyl)phenyl)-2-methylpropan-1-one were mixed with 0.25 mL of Et₃N and 5 mg of N,N-dimethylpyridin-4-amine in 5 mL of dichloromethane. The mixture was stirred at room temperature for 3 hrs and then diluted by 20 mL of Et₂O. The mixture was washed by saturated NaHCO₃ of equal volume. The separated aqueous layer was acidized to pH=2, and then extracted twice with ethyl acetate of equal volume. The combined organic layer was dried and concentrated, and the crude product was further purified by silica gel column chromatography with mixtures of hexane/ethyl acetate (V/V=1/1) to give the target products A and B as colorless oil (91% yield, and A/B=2/1). ¹H NMR (MeOD, ppm): 7.99 (s, 2H), 7.94 (s, 2H), 7.87-7.78 (m, 2H), 7.64-7.39 (m, 8H), 5.41-5.39 (br, 4H), 1.52-1.49 (m, 12H); ¹³C NMR (MeOD, ppm): 210.7, 204.6, 193.5, 193.4, 193.2, 193.1, 169.3, 168.2, 167.6, 167.4, 166.8, 143.1, 136.7, 135.6, 135.5, 132.5, 132.2, 132.1, 132.0, 131.9, 131.8, 131.6, 130.3, 129.9, 129.6, 129.5, 129.4, 129.1, 128.6, 128.4, 128.3, 128.1, 127.3, 127.2, 125.2, 125.1, 125.0, 124.9, 78.2, 77.8, 77.5, 77.1, 67.5, 67.4, 67.0, 27.0.

EXAMPLE 18

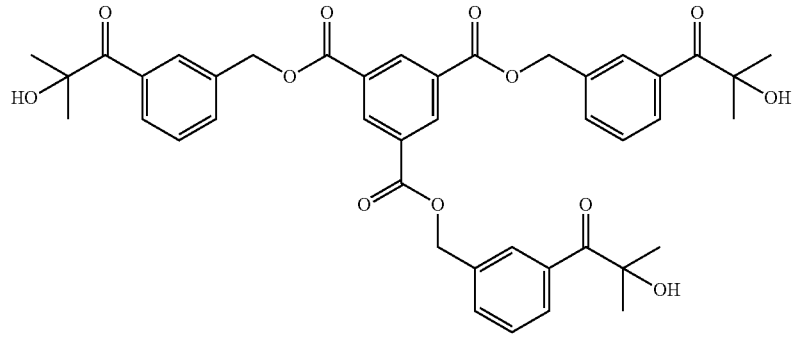 [SMILES: CC(C)(O)C(=O)c1cccc(COC(=O)c2cc(C(=O)OCc3cccc(C(=O)C(C)(C)O)c3)cc(C(=O)OCc3cccc(C(=O)C(C)(C)O)c3)c2)c1]

Under nitrogen atmosphere 1.25 grams of benzene-1,3,5-tricarbonyl trichloride dissolved in 5 mL of dry dichloromethane was added dropwise to a pre-cooled 20 mL of dichloromethane solution at 0° C. containing 2.74 grams of 2-hydroxy-1-(3-(hydroxymethyl)phenyl)-2-methylpropan-1-one, 2 mL of Et₃N and 50 mg of N,N-dimethylpyridin-4-amine. The mixture was stirred for 2 hrs and gradually warmed to room temperature. The mixture was concentrated and then diluted by 100 mL of ethyl acetate, washed successively by saturated NaHCO₃ and brine of half volume. The organic layer was dried and concentrated, and the crude product was further purified by silica gel column chromatography with mixtures of hexane/ethyl acetate (V/V=2/1) to give the target product as colorless oil (97% yield). ¹H NMR (CDCl₃, ppm): 8.88 (s, 3H), 8.15 (s, 3H), 8.01 (d, 3H, J=7.8 Hz), 7.62 (d, 3H, J=7.5 Hz), 7.46 (dd, 3H, J=7.8 Hz, J=7.5 Hz), 5.43 (s, 6H), 4.02 (s, 3H), 1.59 (s, 18H); ¹³C NMR (CDCl₃, ppm): 204.2, 164.6, 135.8, 134.9, 134.5, 132.6, 131.1, 129.8, 129.7, 128.8, 76.8, 66.9, 28.3.

EXAMPLE 19

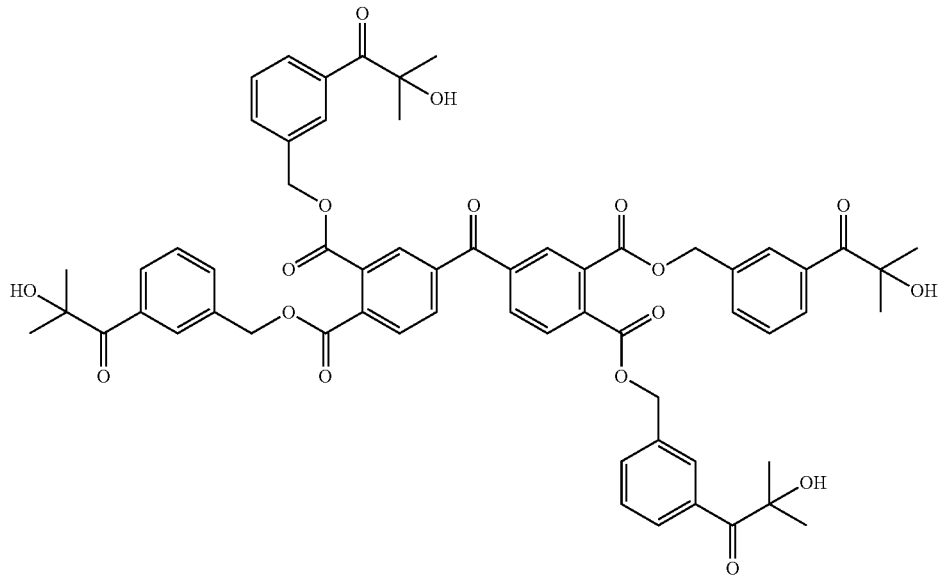 [SMILES: CC(C)(O)C(=O)c1cccc(COC(=O)c2ccc(C(=O)c3ccc(C(=O)OCc4cccc(C(=O)C(C)(C)O)c4)c(C(=O)OCc4cccc(C(=O)C(C)(C)O)c4)c3)cc2C(=O)OCc2cccc(C(=O)C(C)(C)O)c2)c1]

Similar to the procedure already described above in Example 18, the target product was prepared in 5.9 grams, 93% isolated yield from the reaction of 4.7 grams 2-hydroxy-1-(3-(hydroxymethyl)phenyl)-2-methylpropan-1-one and 2.60 grams of 4,4'-carbonyldiphthaloyl dichloride. $^1$H NMR (CDCl$_3$, ppm): 8.03 (s, 2H), 8.01-7.97 (m, 8H), 7.901 (d, 2H, J=8.0 Hz), 7.83 (d, 2H, J=7.6 Hz), 7.58-7.47 (m, 4H), 7.45-7.40 (m, 4H), 5.31 (s, 4H), 5.28 (s, 4H), 1.59 (s, 12H), 1.57 (s, 12H); $^{13}$C NMR (CDCl$_3$, ppm): 204.3, 204.2, 192.8, 166.5, 165.8, 138.6, 135.8, 135.4, 134.5, 132.7, 132.6, 131.7, 130.4, 129.8, 129.7, 129.6, 129.3, 128.7, 76.8, 67.3, 67.2, 28.3, 28.2.

EXAMPLE 20

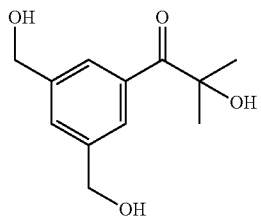 [SMILES: CC(C)(O)C(=O)c1cc(CO)cc(CO)c1]

Under nitrogen atmosphere 261 mg of 1-(3,5-bis(chloromethyl)phenyl)-2-hydroxy-2-methylpropan-1-one that was prepared previously as compound A in the case of Example 9 was mixed with 840 mg of LiOH in 150 mL of water. The mixture was warmed to 80° C. and stirred for 2 hrs, cooled to room temperature, and then extracted with 50 mL of ethyl acetate for six times. The combined organic layer was dried over Na$_2$SO$_4$ and concentrated, and the crude product was further purified by silica gel column chromatography with mixtures of hexane/ethyl acetate (V/V=½) to give the target product as white powder. $^1$H NMR (CDCl$_3$, ppm): 7.99 (s, 2H), 7.48 (s, 1H), 5.32 (t, 2H, J=5.6 Hz), 4.55 (d, 4H, J=5.6 Hz), 3.43 (s, 1H), 1.42 (s, 6H); $^{13}$C NMR (CDCl$_3$, ppm): 204.8, 142.6, 135.5, 128.8, 126.8, 77.1, 63.2, 28.5.

EXAMPLE 21

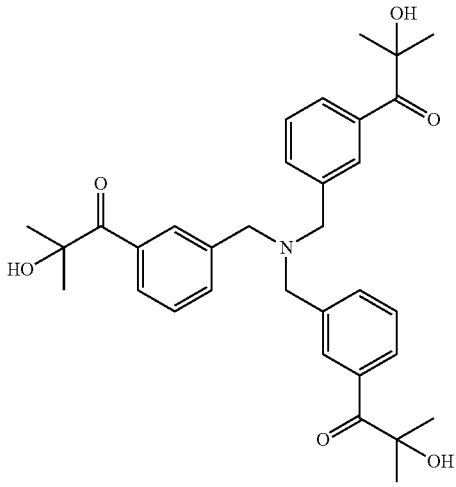 [SMILES: CC(C)(O)C(=O)c1cccc(CN(Cc2cccc(C(=O)C(C)(C)O)c2)Cc2cccc(C(=O)C(C)(C)O)c2)c1]

To a flask containing 100 mg of 1-(3-(chloromethyl)phenyl)-2-hydroxy-2-methylpropan-1-one and 0.1 mL of 25% wt concentration of NH$_3$ aqueous solution was added 3 mg of Bu$_4$NBr. The mixture was stirred at 60° C. for 4 hrs and then diluted by 10 mL of dichloromethane. The solution was washed twice by water of equal volume, dried over Na$_2$SO$_4$, and further purified by silica gel column chromatography with mixtures of hexane/ethyl acetate (V/V=2/1) to give the target product as colorless oil (74% yield). $^1$H NMR (CDCl$_3$, ppm): 8.11 (s, 3H), 7.86 (d, 3H, J=8.0 Hz), 7.55 (d, 3H, J=7.6 Hz), 7.37 (dd, 3H, J=8.0 Hz, J=7.6 Hz), 4.45 (br, 3H), 3.61 (s, 6H), 1.57 (s, 18H); $^{13}$C NMR (CDCl$_3$, ppm): 204.7, 139.5, 134.2, 133.1, 130.1, 128.6, 128.4, 76.8, 57.9, 28.4. HRMS: C$_{33}$H$_{40}$NO$_4$ (M+H), theoretical 546.2850; experimental 546.2726.

EXAMPLE 22

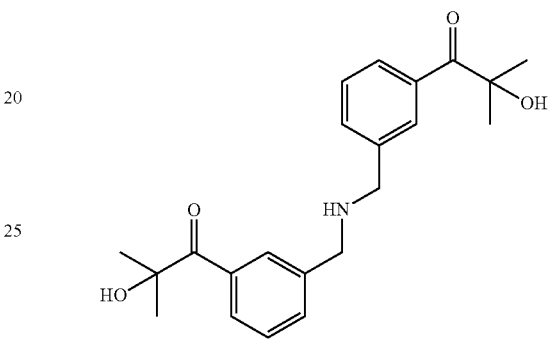

The present target compound was simultaneously formed and isolated from Example 21 described above in 18% yield. $^1$H NMR (CDCl$_3$, ppm): 8.13 (s, 2H), 7.88 (d, 2H, J=8.1 Hz), 7.65 (d, 2H, J=7.6 Hz), 7.44 (dd, 2H, J=8.1 Hz, J=7.6 Hz), 3.66 (s, 4H), 1.58 (s, 12H).

EXAMPLE 23

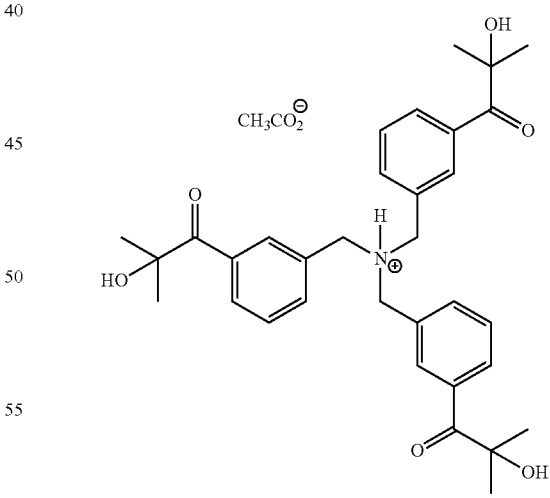

The present target product was readily prepared by mixing 54.5 mg of the compound synthesized in Example 21 and 6 mg of acetic acid in 1.5 mL of chloroform. $^1$H NMR (CDCl$_3$, ppm): 8.11 (s, 3H), 7.87 (d, 3H, J=8.0 Hz), 7.56 (d, 3H, J=7.6 Hz), 7.39 (dd, 3H, J=8.0 Hz, J=7.6 Hz), 5.27 (s, 3H), 3.64 (s, 6H), 2.04 (s, 3H), 1.60 (s, 18H); $^{13}$C NMR (CDCl$_3$, ppm): 204.8, 176.3, 139.5, 134.1, 133.2, 130.1, 128.6, 128.4, 57.9, 53.5, 28.4, 20.7.

EXAMPLE 24

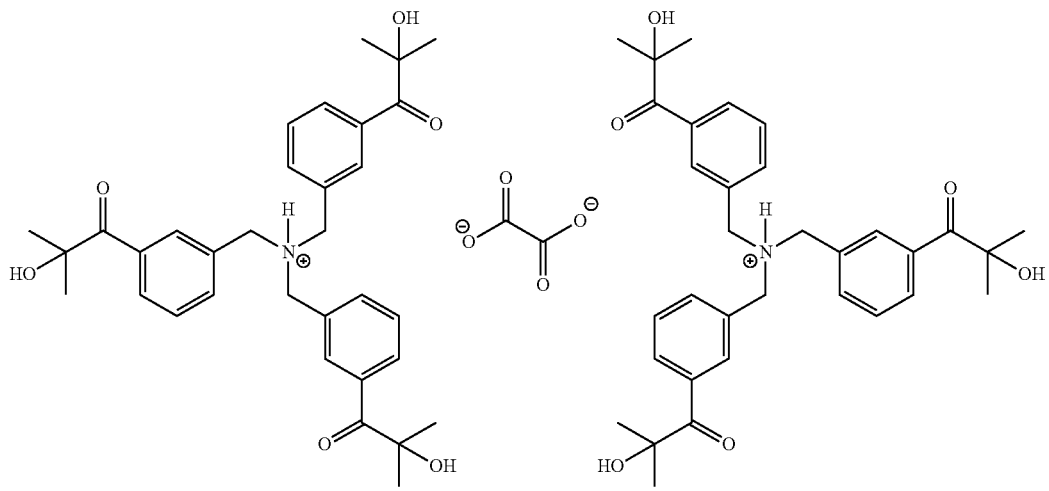 [SMILES: CC(C)(O)C(=O)c1cccc(C[NH+](Cc2cccc(C(=O)C(C)(C)O)c2)Cc2cccc(C(=O)C(C)(C)O)c2)c1 ; O=C([O-])C(=O)[O-] ; CC(C)(O)C(=O)c1cccc(C[NH+](Cc2cccc(C(=O)C(C)(C)O)c2)Cc2cccc(C(=O)C(C)(C)O)c2)c1]

The present target product was quantitatively prepared by mixing 42 mg of the compound synthesized in Example 21 and 3.5 mg of oxalic acid in 1.5 mL of $D_2O$. $^1H$ NMR ($D_2O$, ppm): 7.90 (d, 6H, J=7.6 Hz), 7.74 (s, 6H), 7.46-7.39 (m, 12H), 4.43 (s, 2H), 1.41 (s, 36H); $^{13}C$ NMR ($D_2O$, ppm): 207.6, 164.2, 135.7, 135.0, 131.5, 130.7, 129.4, 129.3, 77.7, 58.1, 26.9.

EXAMPLE 25

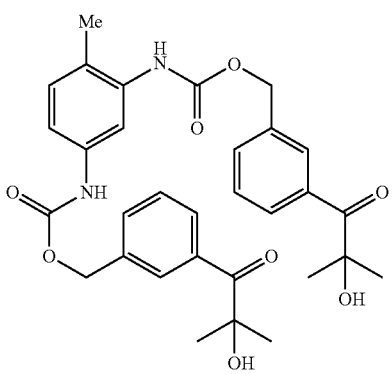 [SMILES: Cc1ccc(NC(=O)OCc2cccc(C(=O)C(C)(C)O)c2)cc1NC(=O)OCc1cccc(C(=O)C(C)(C)O)c1]

To a flask containing 466 mg of 2-hydroxy-1-(3-(hydroxymethyl)phenyl)-2-methylpropan-1-one and 174 mg of 2,4-diisocyanato-1-methylbenzene in 8 mL of butyl acetate was added 0.02 mL of activator dibutyltin dilaurate. The mixture was heated at 80° C. for 3 hrs and the concentrated crude was directly purified by silica gel column chromatography with mixtures of hexane/ethyl acetate (V/V=1/1) to give the target product as colorless oil. HRMS: $C_{31}H_{35}N_2O_8$ (M+H), theoretical 563.2393; Experimental 563.2389.

EXAMPLE 26

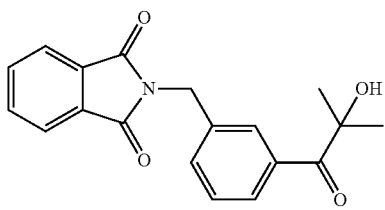 [SMILES: CC(C)(O)C(=O)c1cccc(CN2C(=O)c3ccccc3C2=O)c1]

A mixture containing 74 mg of phthalimide, 69 mg of $K_2CO_3$, and 160 mg of 1-(3-(chloromethyl)phenyl)-2-hydroxy-2-methylpropan-1-one in 1 mL of dry DMF was heated at 95° C. for 10 hrs. The mixture was diluted by 10 mL of water, and extracted three times each with 8 mL of ethyl acetate. The combined organic layer was dried over $Na_2SO_4$, filtered, and the concentrated crude was purified by silica gel column chromatography with mixtures of hexane/ethyl acetate (V/V=5/1) to give 130 mg of the target product as colorless oil (81% yield). $^1H$ NMR ($D_2O$, ppm): 8.10 (s, 1H), 7.91 (d, 1H, J=8.0 Hz), 7.80 (m, 2H), 7.67 (m, 2H), 7.58 (d, 1H, J=7.6 Hz), 7.38 (dd, 1H, J=8.0 Hz, J=7.6 Hz), 4.85 (s, 2H), 4.14 (s, 1H), 1.58 (s, 6H); $^{13}C$ NMR ($D_2O$, ppm): 204.3, 167.9, 136.7, 134.3, 134.1, 133.0, 131.9, 131.0, 129.2, 128.8, 123.4, 76.5, 41.3, 28.3.

EXAMPLE 27

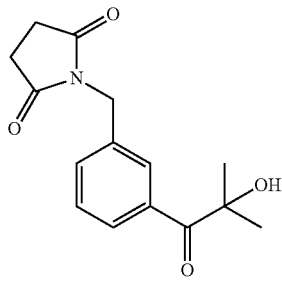 [SMILES: CC(C)(O)C(=O)c1cccc(CN2C(=O)CCC2=O)c1]

A mixture containing 50 mg of succinimide, 69 mg of $K_2CO_3$, and 160 mg of 1-(3-(chloromethyl)phenyl)-2-hydroxy-2-methylpropan-1-one in 1 mL of dry DMF was heated at 95° C. for 18 hrs. The mixture was diluted by 10 mL of water, and extracted three times each with 8 mL of ethyl acetate. The combined organic layer was washed by brine for three times, dried over $Na_2SO_4$, filtered, and the concentrated crude was purified by silica gel column chromatography with mixtures of hexane/ethyl acetate (V/V=5/1) to give 96 mg of the target product as colorless oil (70% yield). $^1$H NMR ($D_2O$, ppm): 8.01 (s, 1H), 7.90 (d, 1H, J=8.0 Hz), 7.52 (d, 1H, J=7.6 Hz), 7.36 (dd, 1H, J=8.0 Hz, J=7.6 Hz), 4.64 (s, 2H), 4.09 (s, 1H), 2.67 (s, 4H), 1.56 (s, 6H); $^{13}$C NMR ($D_2O$, ppm): 204.3, 176.9, 136.0, 134.3, 133.2, 130.1, 129.2, 128.8, 77.5, 76.5, 42.1, 28.3.

EXAMPLE 28

UV-Curing Applications

The acrylates-based sample materials were formulated below (% wt):

UCB Ebecry 605 (30%), UCB Ebecryl 7100 (8%), Jiangsu Sanmu PO3-GTA (30%), Sartomer hexamethylene diacrylate (24%), Evonik acrylated polysiloxane Tego Rad 2100 (0.5%), Sartomer SR 494 ethoxylated pentaerythritol tetraacrylate (3.5%), photo-initiator (4%).

The material was spray-coated onto a cardboard to form a layer of about 20 μm thickness, UV-curing experiments were conducted with two 80 W medium-pressure Hg lamps as light source associated with a variable-speed conveyor belt, the curing speed was the maximum conveyor belt speed (m/min) recorded at which a complete curing of the coated layer was determined by the fingernail resistance test. The residual odor of each of the experimentally cured material, as a measure of VOCs emission in the experiments, was evaluated independently by 5 individuals, whose ratings were classified using the following numerical indicators:

Level 0: no odor detected at all,
Level 1: very light odor detected,
Level 2: light odor detected,
Level 3: some odor detected,
Level 4: significant odor detected,
Level 5: strong odor detected.

The results obtained on samples containing 12 different photo-initiator compounds and a comparison photo-initiator (i.e., the conventional Darocur 1173) were compiled in the following table.

| Photo-initiator | Curing Speed (m/min) | Residual Odor Rating |
|---|---|---|
| Example 1 | 90 | 0 |
| Example 3 | 50 | 1 |
| Example 5 | 60 | 0-1 |
| Example 6 | 60 | 1-2 |
| Example 7 | 70 | 0 |
| Example 8 | 80 | 0-1 |
| Example 11 | 100 | 0 |
| Example 12 | 90 | 0-1 |
| Example 17 | 60 | 0 |
| Example 18 | 110 | 0 |
| Example 19 | 90 | 0 |
| Example 21 | 80 | 0 |
| Darocur 1173 | 70 | 4 |

These results clearly demonstrated that compounds disclosed in this invention are effective photo-initiators for photo-polymerizations of ethylenically unsaturated systems, and moreover while achieving so, as compared to conventional benchmark Darocur 1173, they generally displayed higher or comparable initiation activities and no or very low levels of residual odor. These properties are critically important for formulating high-performance radiation-curable materials that can offer valuable environmental and economic benefits and health-friendliness.

It should be emphasized that while the invention had been described above with reference to various specific illustrative but not limiting embodiments thereof, it is apparent to practitioners in the field that many readily conceivable modifications, changes, and variations, particularly in the linking units connecting such meta-substituted aryl hydroxyketones in multi- or poly-functional hydroxyketone photo-initiators, can be made without departing from the inventive concept and core structural features that had already been defined herein. Accordingly, it is intended to embrace all such possible modifications, changes, and variations that fall within the spirit and broad scope defined in the claims associated with this invention.

What is claimed is:

1. A compound is selected from the following formula (I), formula (II) and formula (III):

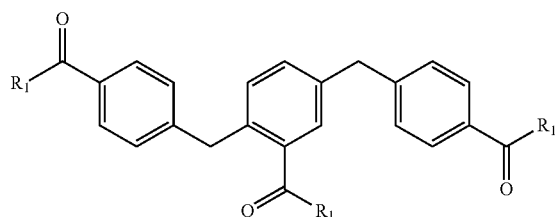

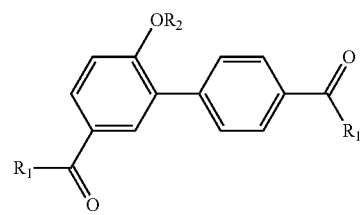

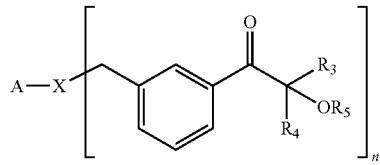

wherein $R_1$ is selected from

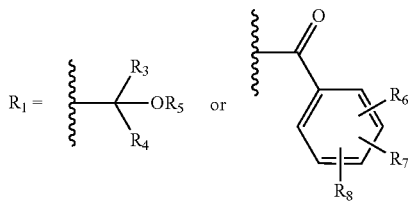

$R_2$, $R_3$, and $R_4$ are independently selected from $C_1$-$C_{12}$ alkyl which may be branched or unbranched, may or may not contain ring structures, or independently selected from $C_6$-$C_{12}$ aryl ring which may be substituted or unsubstituted, which may be independently interrupted by one to four groups selected from O, N, Si, S, C(O), C(S), OC(O), OC(O)O, SC(O), SC(S), C(O)NH, C(O)NR$_x$, OP(O), OSiR$_x$R$_y$O, or carbon-carbon double or triple bond;

R$_5$ is hydrogen, R$_x$, Si(R$_x$)$_2$(R$_y$), or Si(R$_x$)$_3$; R$_6$, R$_7$, and R$_8$ are independently selected from hydrogen or R$_x$, wherein R$_x$ or R$_y$ has the similar structure with that of R$_2$, R$_3$, or R$_4$;

n is an integer from 1 to 6;

X is O, S, N, NH, or NR$_x$;

A is a n-valent linkage, A-X is OH, OR$_x$, SR$_x$, NHR$_x$, N(R$_x$)$_2$, or quaternary ammonium cation selected from (R$_x$)$_3$N$^+$ or (R$_x$)$_2$R$_y$N$^+$, when n is 1; A-X is N, NR$_x$, or quaternary ammonium cation selected from R$_x$N$^+$, R$_x$R$_y$N$^+$, or (R$_x$)$_2$N$^+$, when n is 2, 3, 4, 5, or 6; or A-X—(H)$_n$ represents a n-functional alcohol, thiol, phenol, carboxylic acid, or amine, respectively.

2. The compound of claim 1, when A-X—(H)$_n$ is a n-functional alcohol, thiol, phenol, carboxylic acid, or amine which are selected from the following groups:

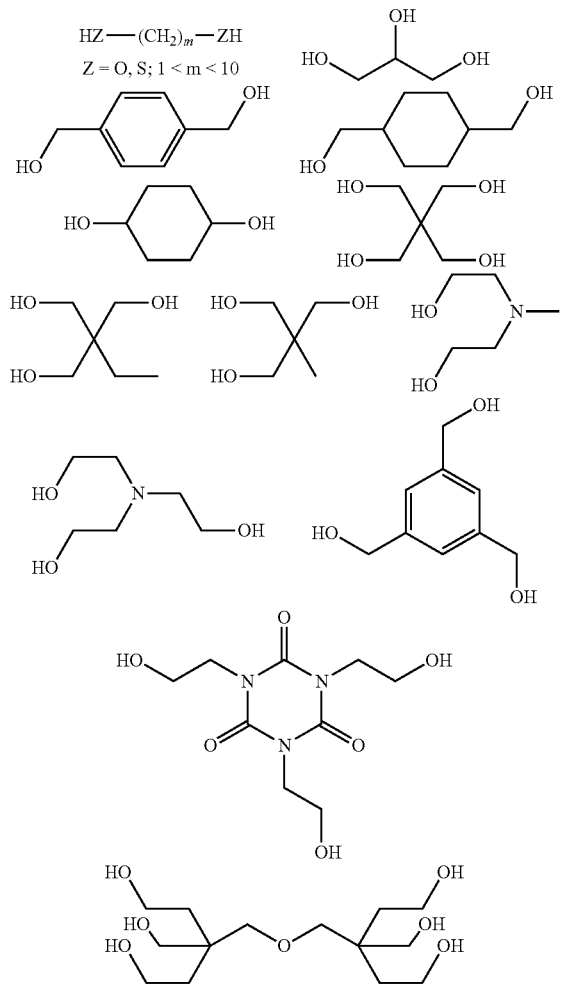

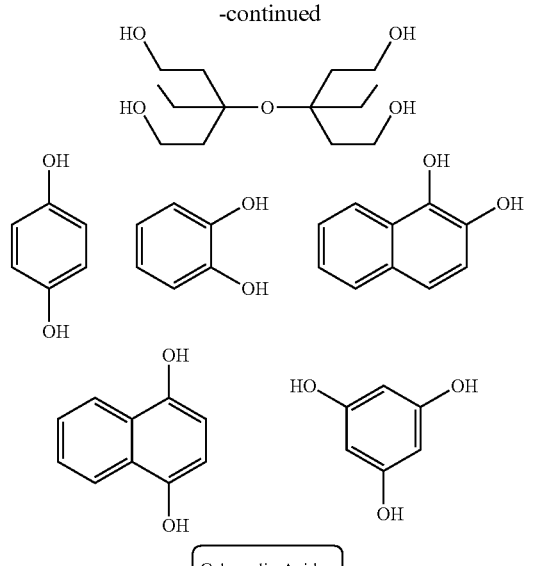

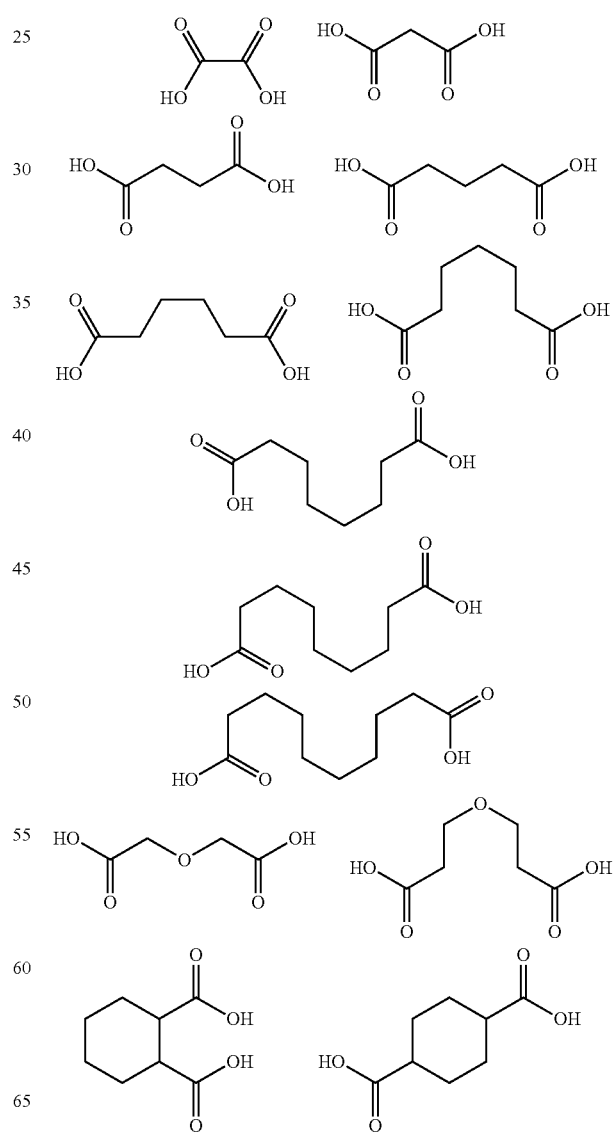

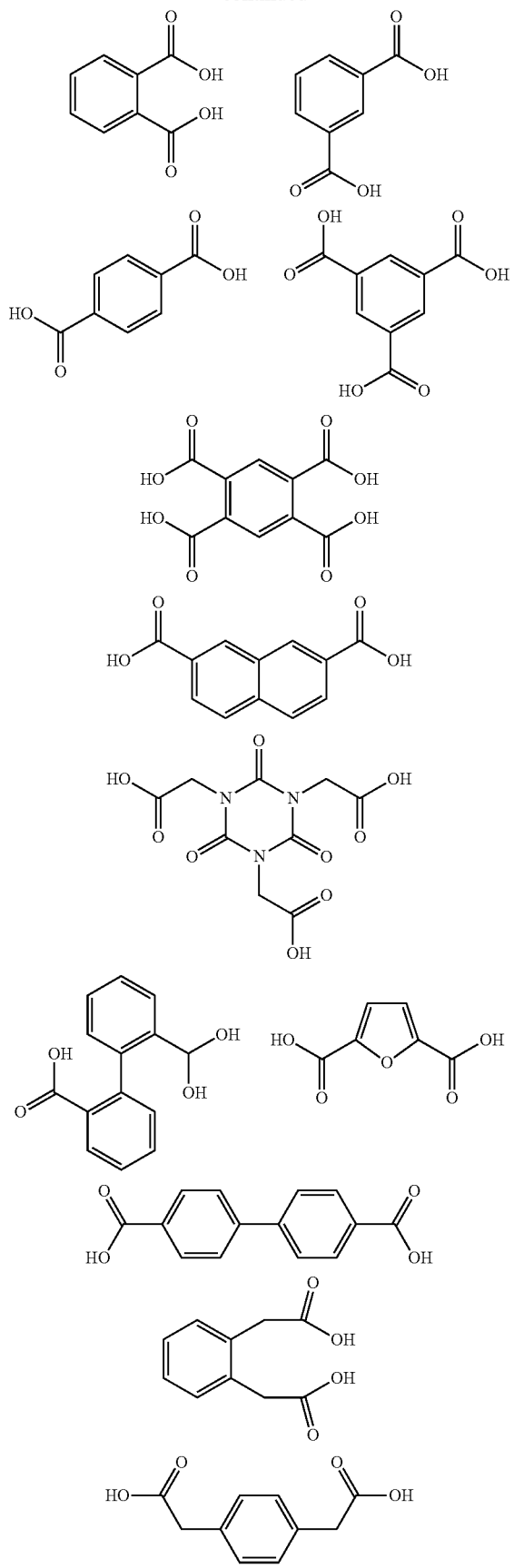
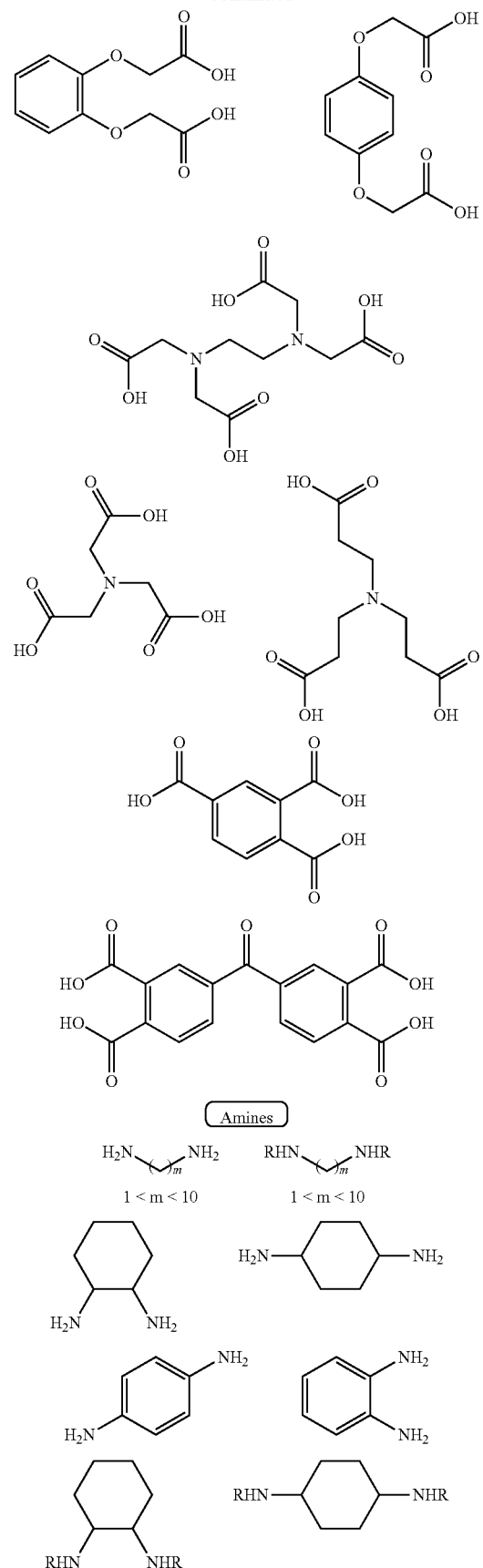

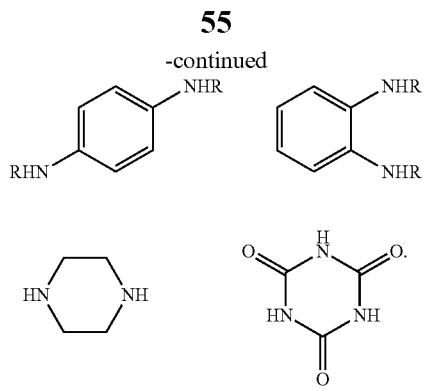
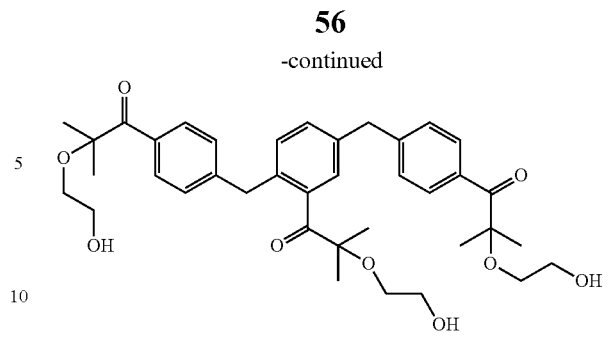
3. The compound of claim 1, the compound of formula (I) is selected from the following structures:
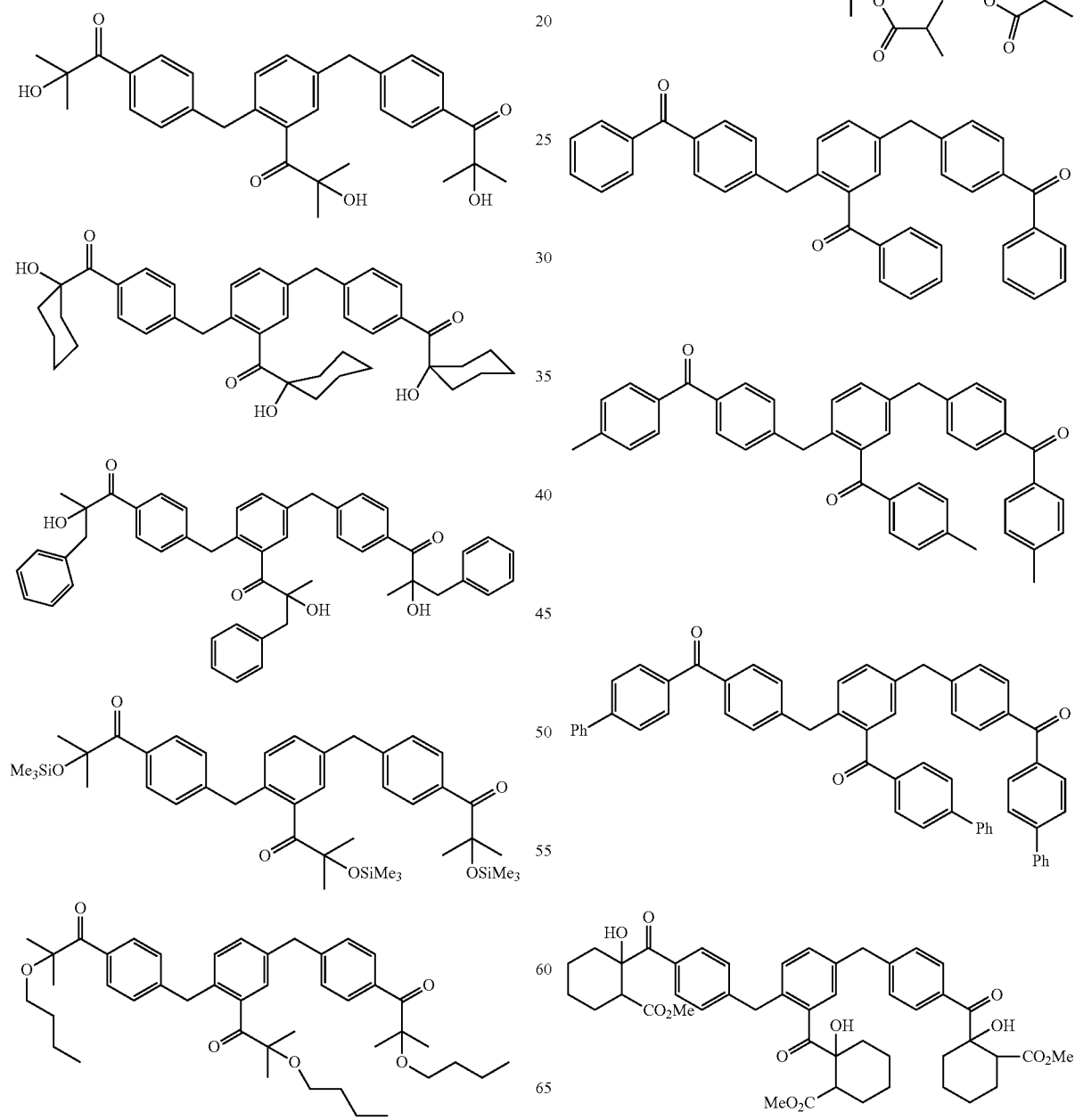

-continued
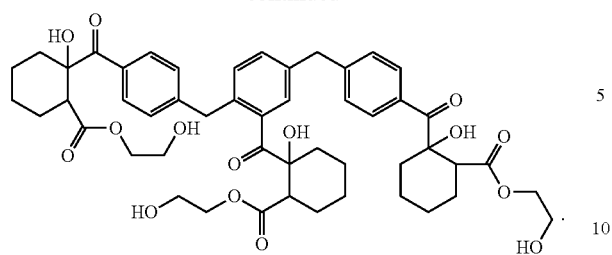
4. The compound of claim 1, the compound of formula (II) is selected from the following structures:
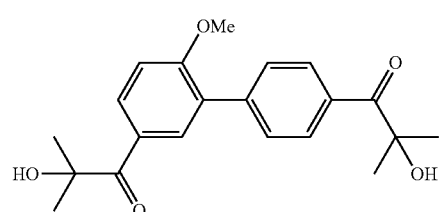
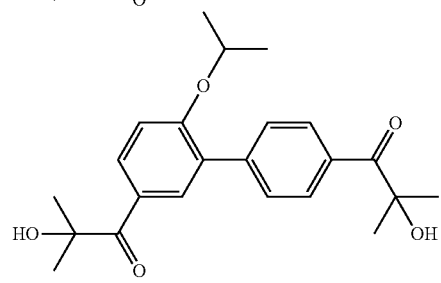
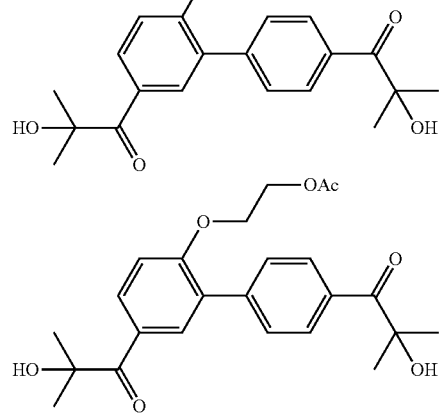
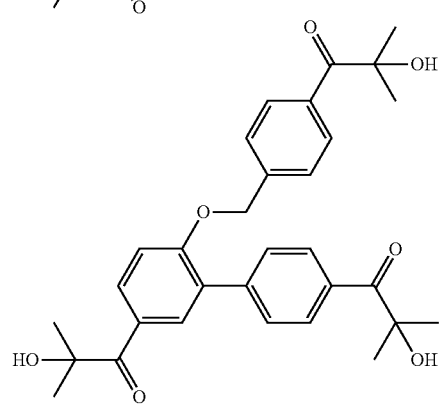
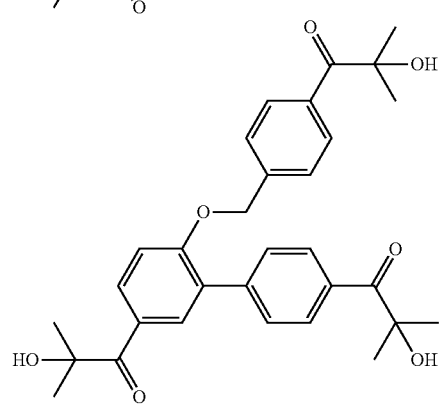
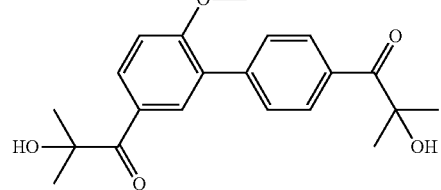
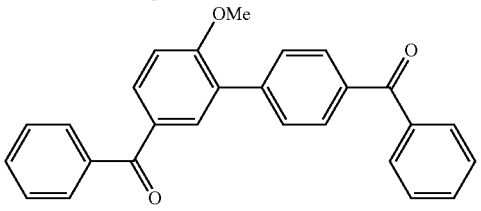
-continued
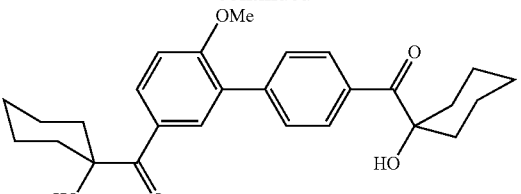
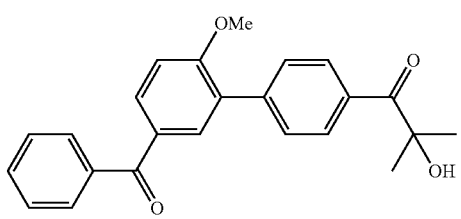
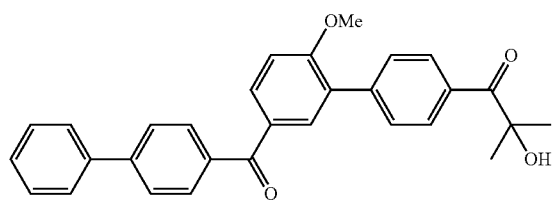
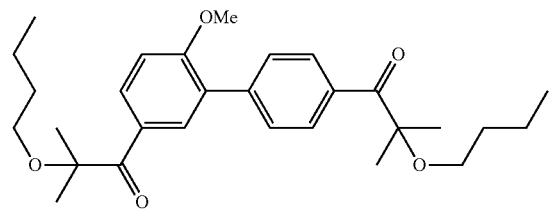
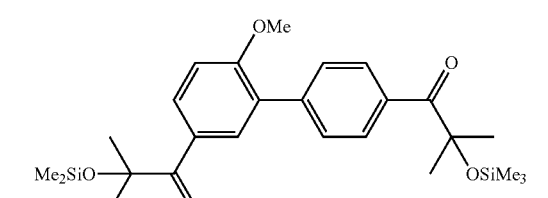
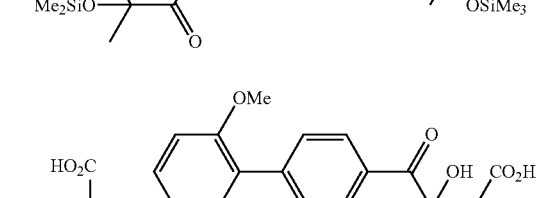
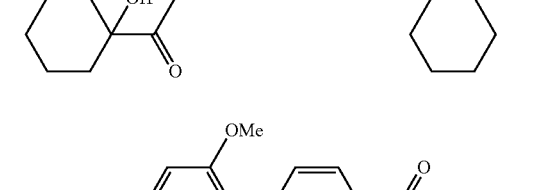
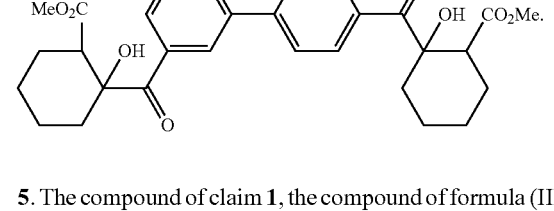
5. The compound of claim 1, the compound of formula (III) is selected from the following structures when n is 1:

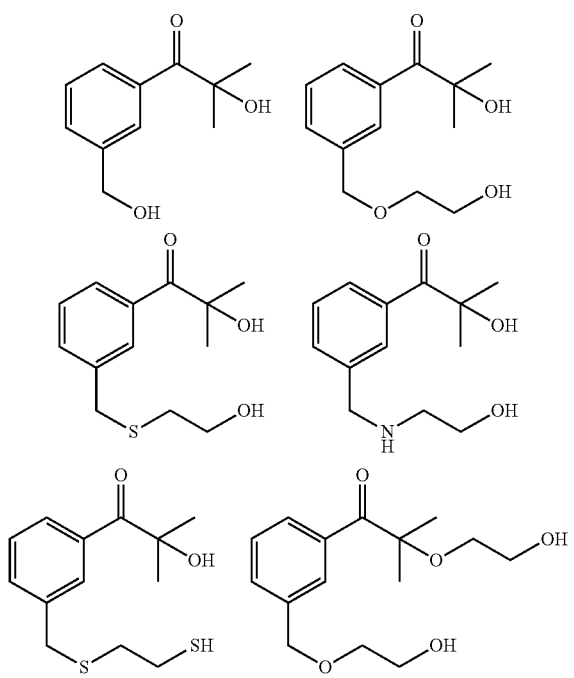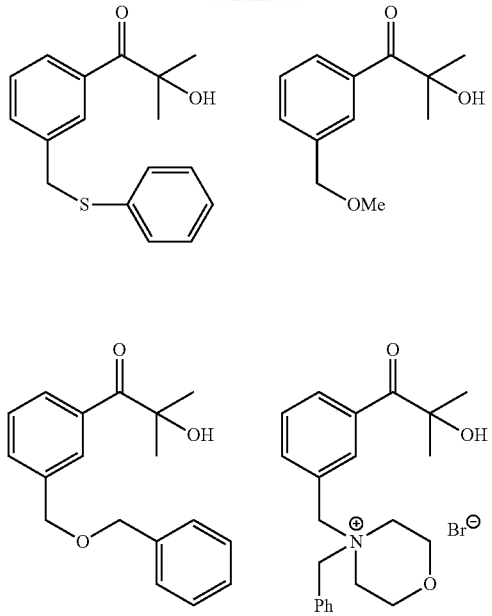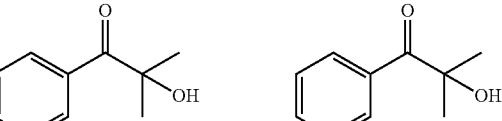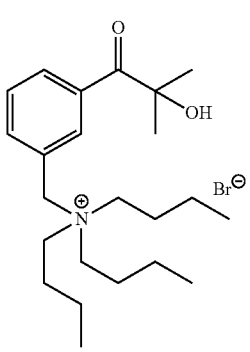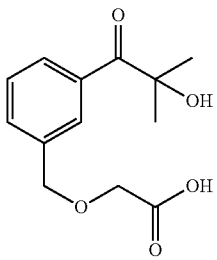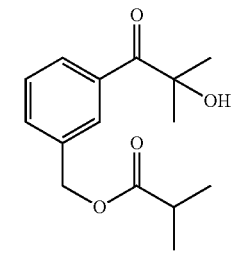

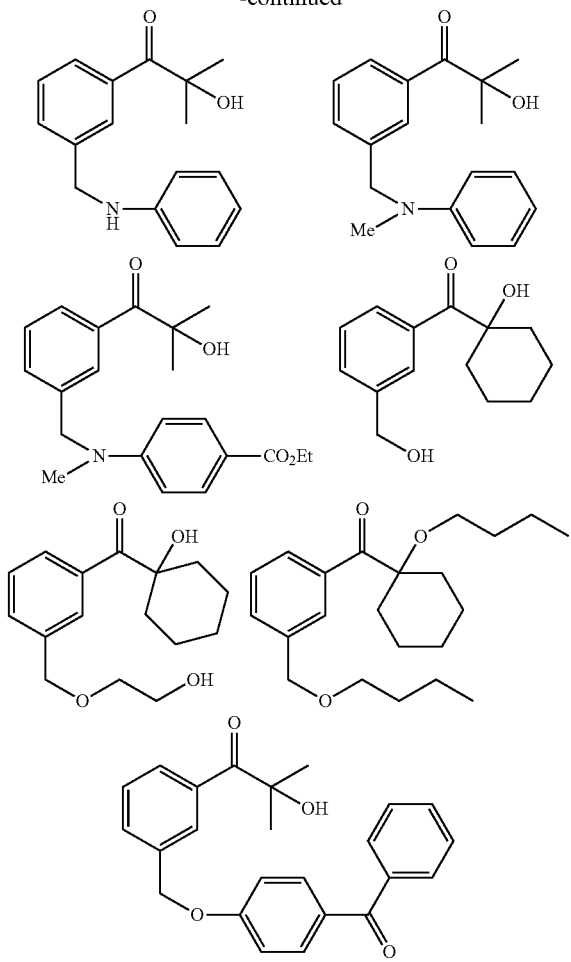
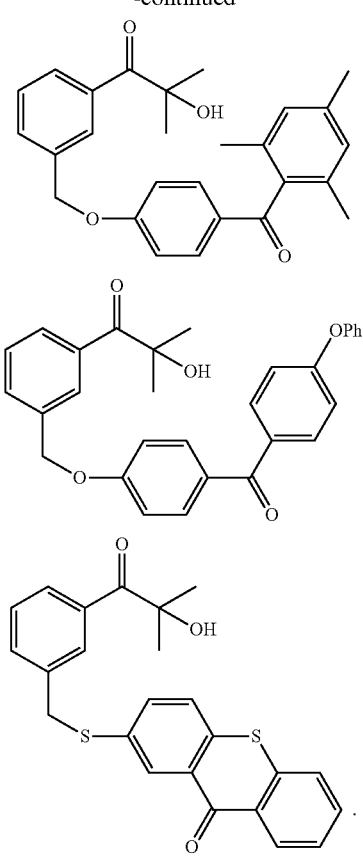
6. The compound of claim 1, the compound of formula (III) is selected from the following structures when n is 2, 3, 4, 5 or 6:
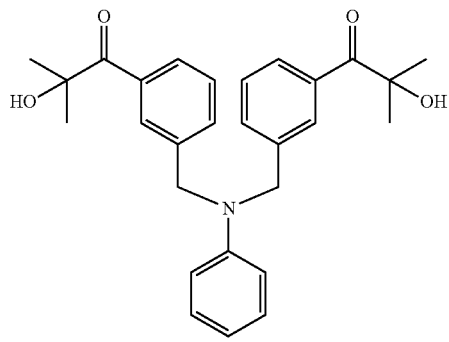
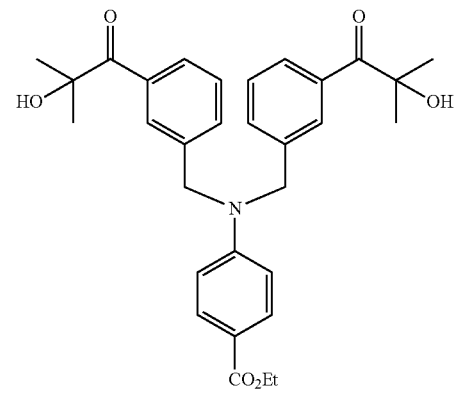
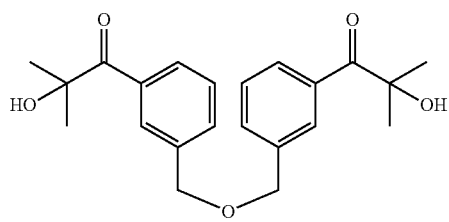
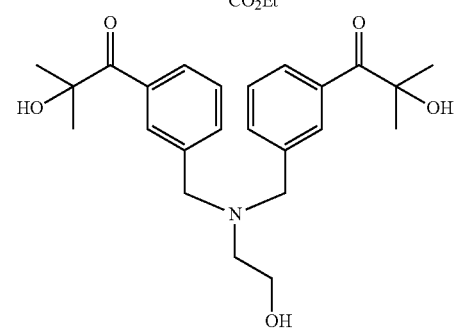

63
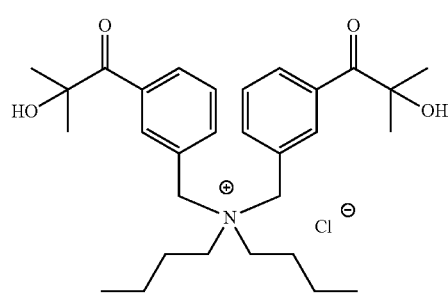
-continued
64
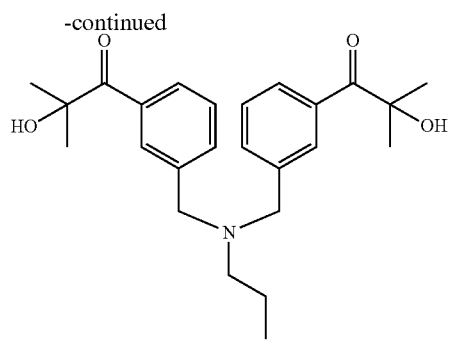
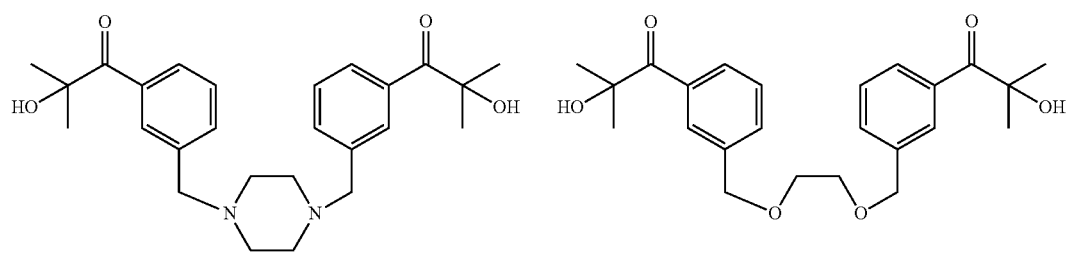
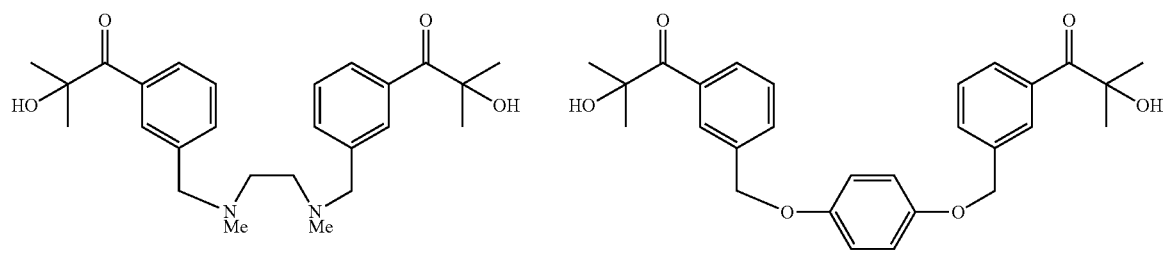
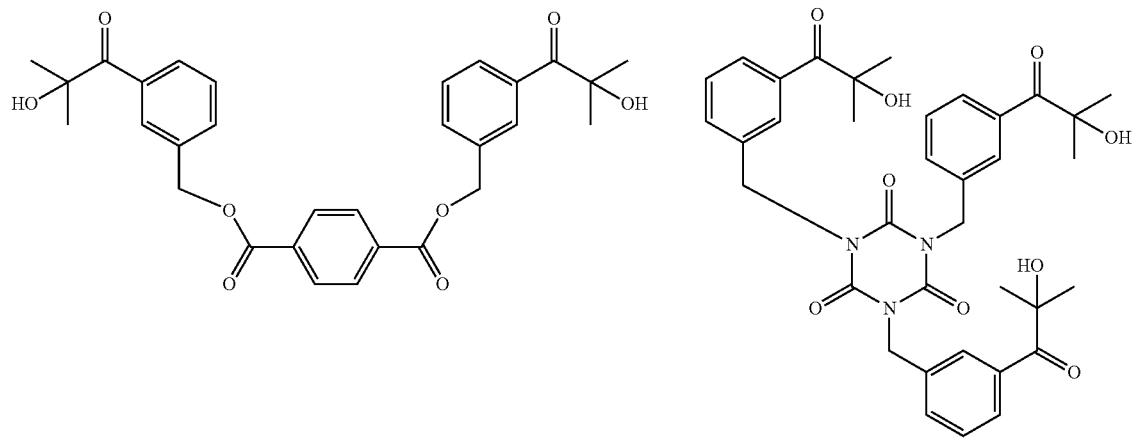
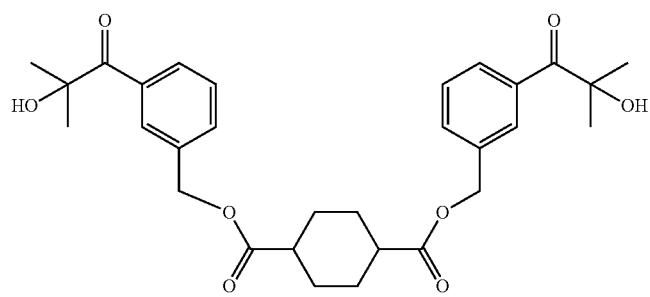

65
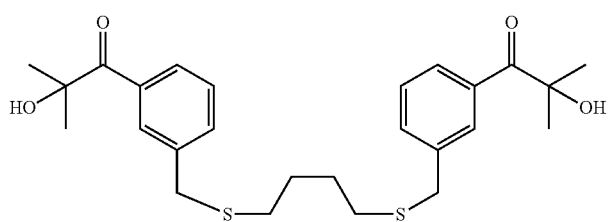
-continued
66
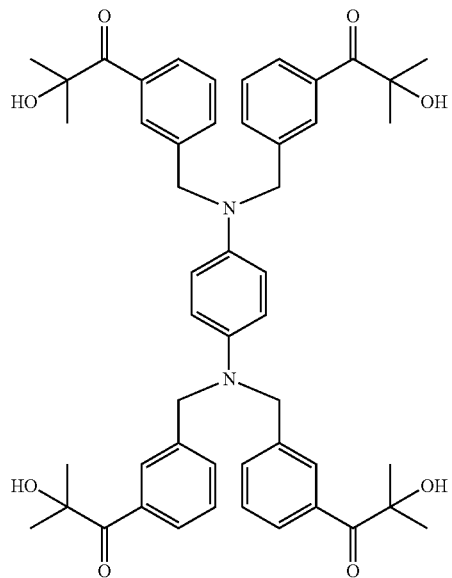
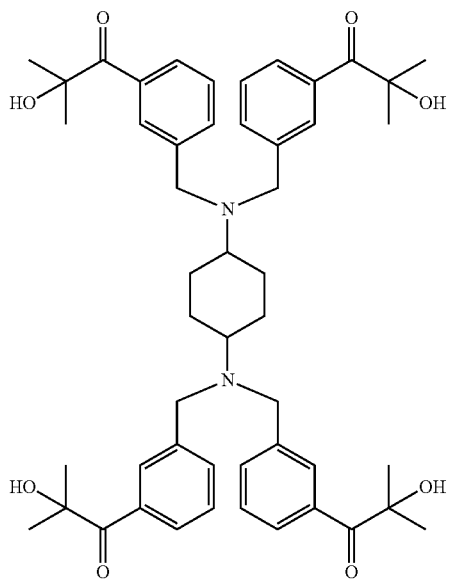
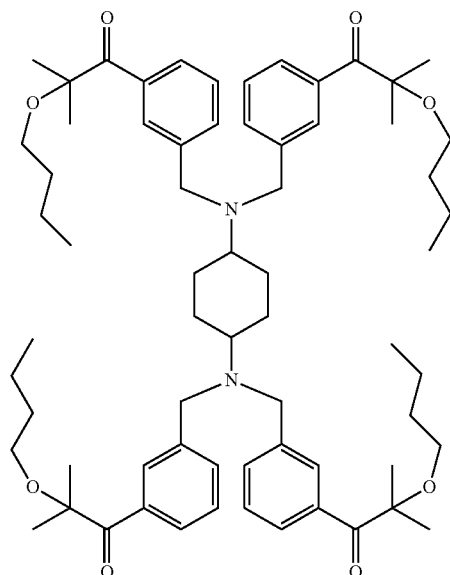
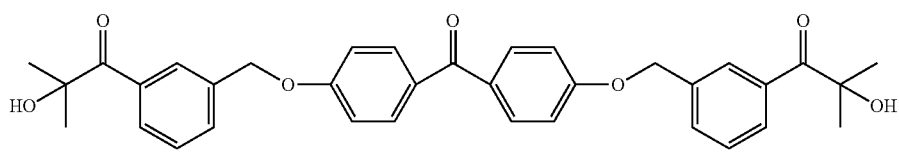
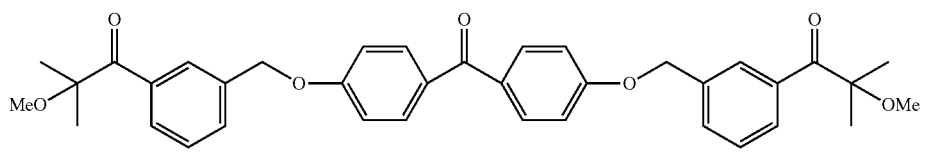

-continued
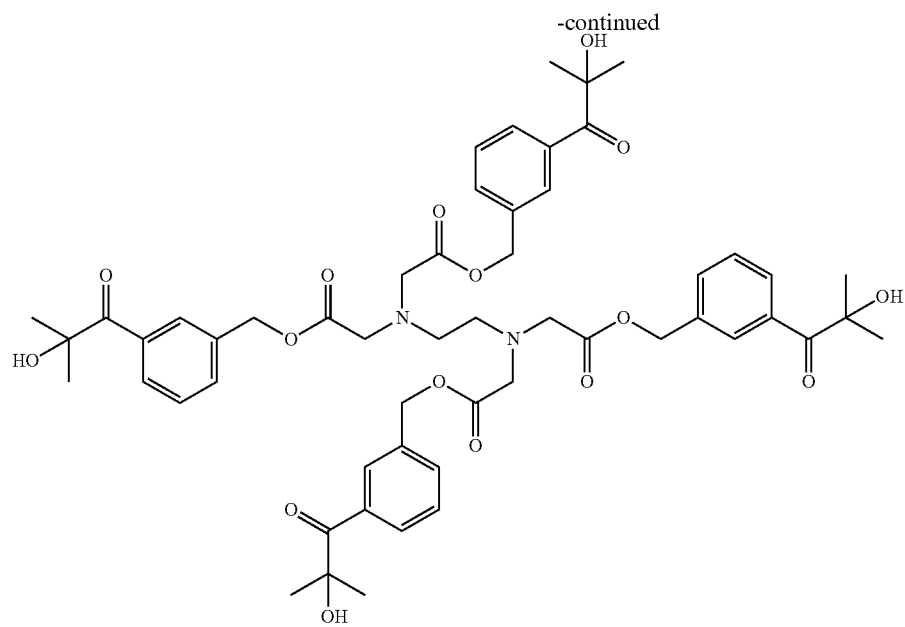
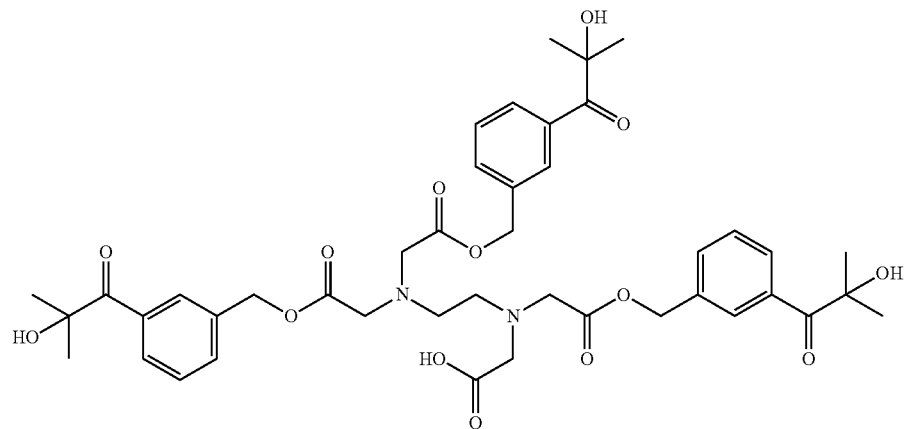
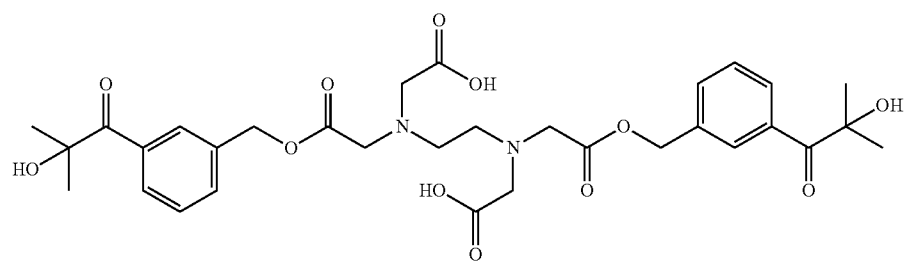

-continued
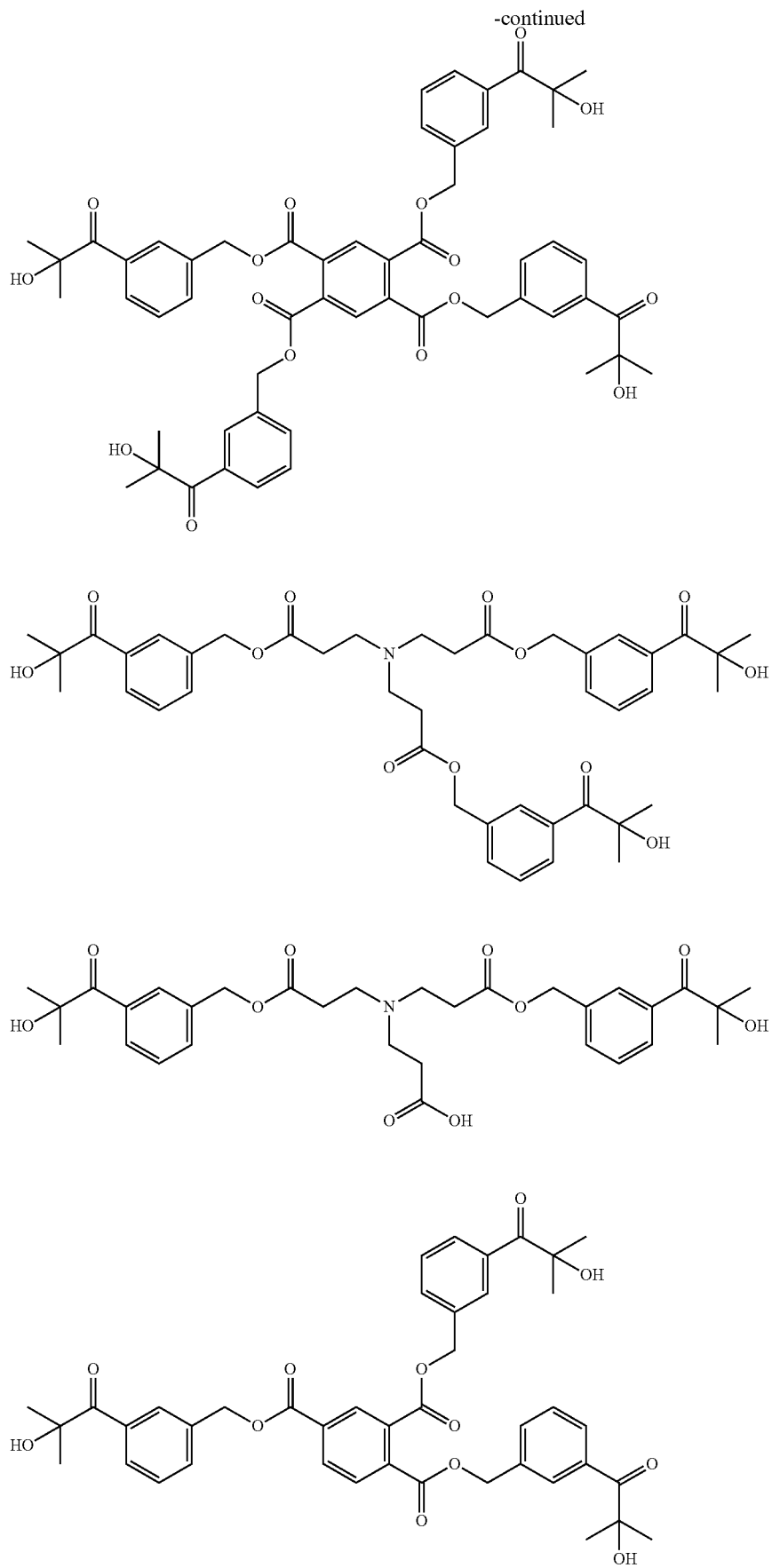

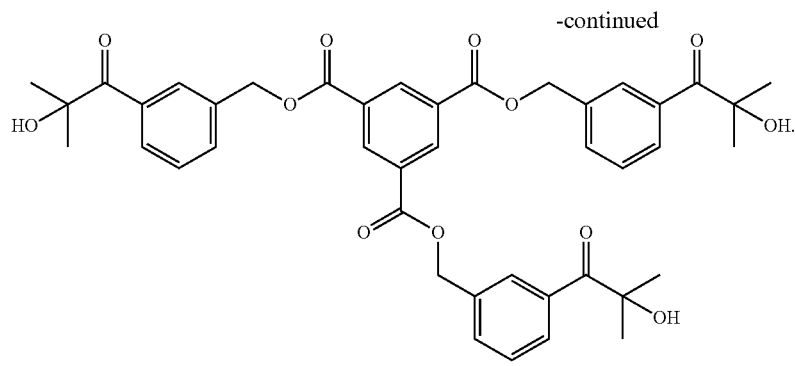

7. A process for preparing the compounds of claim 1, 1,4-dibenzylbenzene or alkyl-substituted 2-phenyl-phenol reacts with acyl donor H in the presence of Lewis acid reagents selected from anhydrous $AlCl_3$, $FeCl_3$, $ZnCl_2$, or $La(OTf)_3$ which results in acylated compounds being able to be used as common intermediate further to prepare formula (I) or formula (II) compounds of claim 1, said acyl donor H is

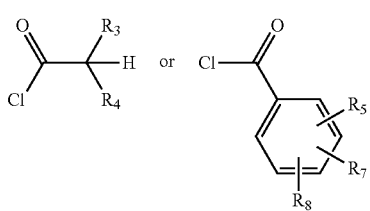

wherein $R_3$, $R_4$, $R_6$, $R_7$ and $R_8$ are as defined in claim 1; the preparation of formula (III) of claim 1, the etherification, esterification, or silylation is performed on the hydroxyl group of following compound F, wherein $R_3$ and $R_4$ are independently selected from $C_1$-$C_{12}$ alkyl which may be branched or unbranched, may or may not contain ring structures, or independently selected from $C_6$-$C_{12}$ aryl ring which may be substituted or unsubstituted, which may be independently interrupted by one to four groups selected from O, N, Si, S, C(O), C(S), OC(O), OC(O)O, SC(O), SC(S), C(O)NH, C(O)NR$_x$, OP(O), OSiR$_x$R$_y$O, or carbon-carbon double or triple bond

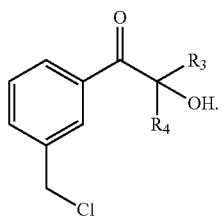

8. The process of claim 7, comprising that a hydroxyketone compound is site-specifically chloromethylated at the meta-position of its electronically deactivated aryl ring through Friedel-Crafts alkylation reaction, yielding a meta-chloromethylated compound as said compound F.

9. The process of claim 8, said hydroxyketone is Darocur 1173.

10. The process of claim 7, the said compound F reacts with a compound selected from $H_2OC$—R, $H_2N$—R, HS—R, HO—R or Br—R which yields the compound formula III of claim 1.

11. A photo-initiator comprising aromatic ketone compound which is selected from the formula (I), (II) or (III) compound of claim 1.

12. The photo-initiator of claim 11, said photo-initiator is able to be a mixture that consists of more than one kind of said aromatic ketone compounds.

13. The photo-initiator of claim 11, said photo-initiator is used for free-radical photopolymerizations of ethylenically unsaturated systems.

14. The photo-initiator of claim 12, said photo-initiator is used for free-radical photopolymerizations of ethylenically unsaturated systems.

* * * * *